(12) United States Patent
Grammenos et al.

(10) Patent No.: US 9,137,997 B2
(45) Date of Patent: Sep. 22, 2015

(54) USE OF SUBSTITUTED DITHIINE-DICARBOXIMIDES FOR COMBATING PHYTOPATHOGENIC FUNGI

(75) Inventors: Wassilios Grammenos, Ludwigshafen (DE); Nadege Boudet, Hemsbach (DE); Richard Riggs, Mannheim (DE); Jochen Dietz, Karlsruhe (DE); Egon Haden, Speyer (DE); Marcus Fehr, Speyer (DE)

(73) Assignee: BASF SE, Ludwigshafen (DE)

( * ) Notice: Subject to any disclaimer, the term of this patent is extended or adjusted under 35 U.S.C. 154(b) by 6 days.

(21) Appl. No.: 14/111,271

(22) PCT Filed: Apr. 10, 2012

(86) PCT No.: PCT/EP2012/056430
§ 371 (c)(1),
(2), (4) Date: Oct. 11, 2013

(87) PCT Pub. No.: WO2012/140001
PCT Pub. Date: Oct. 18, 2012

(65) Prior Publication Data
US 2014/0045687 A1    Feb. 13, 2014

Related U.S. Application Data

(60) Provisional application No. 61/475,735, filed on Apr. 15, 2011.

(30) Foreign Application Priority Data

Apr. 15, 2011    (EP) .................................... 11162712

(51) Int. Cl.
| | | |
|---|---|---|
| *A01N 43/90* | (2006.01) | |
| *C07D 403/04* | (2006.01) | |
| *C07D 405/04* | (2006.01) | |
| *C07D 409/04* | (2006.01) | |
| *C07D 411/04* | (2006.01) | |
| *C07D 413/04* | (2006.01) | |
| *C07D 417/04* | (2006.01) | |
| *C07D 487/04* | (2006.01) | |
| *C07D 491/056* | (2006.01) | |
| *C07D 495/04* | (2006.01) | |
| *C07D 513/04* | (2006.01) | |
| *C09B 57/00* | (2006.01) | |

(52) U.S. Cl.
CPC .............. *A01N 43/90* (2013.01); *C07D 403/04* (2013.01); *C07D 405/04* (2013.01); *C07D 409/04* (2013.01); *C07D 411/04* (2013.01); *C07D 413/04* (2013.01); *C07D 417/04* (2013.01); *C07D 487/04* (2013.01); *C07D 491/056* (2013.01); *C07D 495/04* (2013.01); *C07D 513/04* (2013.01); *C09B 57/00* (2013.01)

(58) Field of Classification Search
None
See application file for complete search history.

(56) References Cited

U.S. PATENT DOCUMENTS

2010/0120884 A1    5/2010    Seitz et al.
2011/0319462 A1   12/2011    Seitz et al.

FOREIGN PATENT DOCUMENTS

WO    WO 2010/043319    4/2010
WO    WO 2011/029551    3/2011

OTHER PUBLICATIONS

Igarashi, Y.; Watanabe, S. "Studies on the preparation and antimicrobial activity of maleimide compounds. V. Preparation of 1,4-benzothiazine-2,3-dicarboximides via intramolecular cyclization of N-substutited 2-[(2-acylaminophenyl)thio]maleimides and investigation of their antibacterial activity." Nippon Kagaku Kaishi (1992), (11), 1392-1396.*
International Search Report dated May 25, 2012, prepared in International Application No. PCT/EP2012/056430.
International Preliminary Report on Patentability dated Oct. 15, 2013, prepared in International Application No. PCT/EP2012/056430.
Augustin, Manifred, et al. "Vergleichende Betrachtungen zum Reaktionsverhalten von 2-Hydroxy-N-aryl-maleinamidaeuremethylest ern und 2-Hydroxy-N-aryl-maleinimiden". Zeitschrift Fuer Chemie. Deutscher Verlag Fuer Grundstoffindustrie Gmbh. Leipzig. De., Jun. 1, 1987, pp. 211-212, vol. 27. No. 6.
Bettinetti, G.F., et al. "Riduzione catalitica dell 'imide e dell'anidride dell'acido chinossalin-2.3-dicarbossilico" . Annali Di Chimica. Societa Chimica Italiana. Rome. It., Jan. 1, 1961, pp. 1102-1112, vol. 51.
El-Sharief, A.M. Sh., et al., "Some reactions with ketne dithioacetals. Part II: Novel synthesis of quinoxaline, pyrazole and pyrrlo [3,4-b]quinoxaline derivatives using ketene dithioacetals as antimicrobial activity", Afinidad, Barcelona, Spain, Jan. 1, 2003, vol. 60, No. 503, p. 81-87.
Katritzky, Alan R., et al., "Novel chromophoric heterocycles based on maleimide and naphthoquinone", Journal of Heterocyclic Chemistry, Jul. 1, 1989, pp. 885-892, vol. 26. No. 4.
Srinivasan, P.R., et al., "Poly(maleimide-amine)s and poly(maleimide-amine)ethers". European Polymer Journal, Pergamon Press Ltd. Oxford. GB, Jan. 1, 1988, pp. 255-258, vol. 1. 24. No. 3.
Wu, Peng et al. et al, "Synthesis of Novel 1.4-Benzoxazine-2.3-Dicarboximides from Maleic Anhydride and Substituted Aromatic Amines". Synthetic Communications, Jan. 1, 2009, pp. 70-84, vol. 39, No. 1.
Zentz, F., et al. "Syntheses. in vitro antibacterial and antifungal activities of a series of N-alkyl. 1.4-dithiines". Farmaco. Societa Chimica Italiana. Pavia. It., Nov. 1, 2005, pp. 944-947, vol. 60. No. 11-12.

* cited by examiner

*Primary Examiner* — Sue Liu
*Assistant Examiner* — Erin Hirt
(74) *Attorney, Agent, or Firm* — Brinks Gilson & Lione

(57) ABSTRACT

The present invention relates to the use of dithiine-dicarboximide compounds of formula I as defined in the description, and the N-oxides, and salts thereof for combating harmful fungi and seed coated with at least one such compound. The invention also relates to novel dithiine-dicarboximides, processes and intermediates for preparing these compounds and also to compositions comprising at least one such compound.

8 Claims, No Drawings

USE OF SUBSTITUTED DITHIINE-DICARBOXIMIDES FOR COMBATING PHYTOPATHOGENIC FUNGI

This application is a National Stage application of International Application No. PCT/EP2012/056430, filed Apr. 10, 2012, which claims the benefit of U.S. Provisional Application No. 61/475,735, filed Apr. 15, 2011, the entire contents of which are hereby incorporated herein by reference. This application also claims priority under 35 U.S.C. §119 to European Patent Application No. 11162712.1, filed Apr. 15, 2011, the entire contents of which is hereby incorporated herein by reference.

The present invention relates to the use of substituted dithiine-dicarboximides and the N-oxides and the salts thereof for combating phytopathogenic fungi, and to seeds treated with at least one such compound. The invention also relates to novel substituted dithiine-dicarboximide compounds, processes for preparing these compounds and to compositions comprising at least one such compound.

The use of certain substituted dithiine-tetracarboximides of the formula

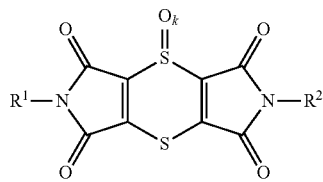

for controlling phytopathogenic fungi is known from WO 2010/043319 and 2011/029551. The compounds according to the present invention differ from those described in the abovemention publications by the specific group fused to one side of the dithiine moiety.

Further, a substituted pyrrolo[3,4-b]quinoxaline-1,3-dione derivative of the formula

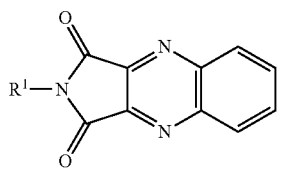

wherein $R^1$ is a substituted phenyl with moderate antifungal activity is disclosed in Affinidad 60(503), 81-87 (2003). The compounds according to the present invention differ from this in the abovementioned publication by the specific $R^1$ substituent as defined herein and only allowing a 4,9-dihydropyrrolo instead of the pyrrolo moiety.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

This object is achieved by the use of certain substituted dithiine-dicarboximides having good fungicidal activity against phytopathogenic harmful fungi.

Accordingly, the present invention relates to the use of compounds of formula I

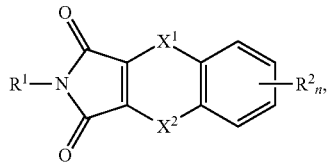

wherein:
$X^1$ is S, S=O, O or NR;
$X^2$ is S, O or NR;
R is hydrogen, $NR^A R^B$, OH, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio, $C_3$-$C_6$-cycloalkyl, $C_3$-$C_6$-cycloalkenyl, $C_3$-$C_6$-cycloalkyl-$C_1$-$C_6$-alkyl, $C_2$-$C_6$-alkenyl, $C_1$-$C_6$-alkylcarbonyl or phenyl;
$R^A$, $R^B$ independently of one another are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_6$-alkylcarbonyl, $C_1$-$C_6$-alkenylcarbonyl, $C_1$-$C_6$-alkynylcarbonyl, $C_1$-$C_6$-alkoxycarbonyl, $C_1$-$C_6$-alkenyloxycarbonyl, $C_1$-$C_6$-alkynyloxycarbonyl, $C_1$-$C_6$-alkylaminocarbonyl, di($C_1$-$C_6$-alkyl)aminocarbonyl, $C_1$-$C_6$-alkenylaminocarbonyl or $C_1$-$C_6$-alkynylaminocarbonyl;
$R^1$ is hydrogen, OH, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio, $C_3$-$C_6$-cycloalkyl, $C_3$-$C_6$-cycloalkenyl, $C_3$-$C_6$-cycloalkyl-$C_1$-$C_6$-alkyl, $C_2$-$C_6$-alkenyl or $C_1$-$C_6$-alkylcarbonyl;
$R^2$ is halogen, OH, CN, nitro, $C_1$-$C_6$-alkyl, $C_1$-$C_6$-alkoxy, $C_3$-$C_6$-cycloalkyl, $C_3$-$C_6$-cycloalkenyl, $C_3$-$C_6$-cycloalkyl-$C_1$-$C_6$-alkyl, $C_2$-$C_6$-alkenyl, $C_2$-$C_6$-alkynyl, $C_1$-$C_6$-alkylcarbonyl, $C_1$-$C_6$-alkenylcarbonyl, $C_1$-$C_6$-alkynylcarbonyl, $C_1$-$C_6$-alkoxycarbonyl, $C_1$-$C_6$-alkenyloxycarbonyl, $C_1$-$C_6$-alkynyloxycarbonyl, $C_1$-$C_6$-alkylaminocarbonyl, di($C_1$-$C_6$-alkyl)aminocarbonyl, $C_1$-$C_6$-alkenylaminocarbonyl or $C_1$-$C_6$-alkynylaminocarbonyl or phenyl;
n is an integer between 0 and 4,
wherein the aliphatic and cyclic groups R, $R^1$ and $R^2$ may carry 1, 2, 3, 4 or up to the maximum possible number of identical or different groups $R^a$:
$R^a$ is amino, halogen, hydroxyl, nitro, CN, carboxyl, $C_1$-$C_4$-alkyl, $C_2$-$C_4$-alkenyl, $C_2$-$C_4$-alkynyl, $C_1$-$C_4$-alkoxy, $C_1$-$C_4$-haloalkoxy, $C_3$-$C_6$-cycloalkyl, $C_3$-$C_8$-cycloalkenyl, $C_1$-$C_6$-alkylamino, $C_1$-$C_4$-alkylcarbonyl, $C_1$-$C_4$-alkoxycarbonyl, $C_1$-$C_4$-alkylcarbonyloxy or $NR^A R^B$;
and the N-oxides and the agriculturally acceptable salts of the compounds of formula I, for combating phytopathogenic fungi.

Further, the preparation of certain substituted pyrrolo-pyrazine-diones, inter alia 4-acetyl-4,9-dihydro-pyrrolo[3,4-b]quinoxaline-1,3-dione (CAS no. 856949-70-7), 2,4-diacetyl-4,9-dihydro-pyrrolo[3,4-b]quinoxaline-1,3-dione (CAS-no. 96954-22-2) and 2,4,9-triacetyl-4,9-dihydro-pyrrolo[3,4-b]quinoxaline-1,3-dione (CAS no. 97470-26-3) has been described in Eur. Polym. J. 24(3), 255-258, (1988); and Annali di Chimica (Rome, Italy) 51, 1102-12, (1961)).

Further, the preparation of certain substituted pyrrolo-oxazine-diones has been described in Synth. Commun. 39(1), 70-84, (2009).

Further, the preparation of certain substituted pyrrolo-thiazine-diones, inter alia 2-methyl-9H-benzo[b]pyrrolo[3,4-e][1,4]thiazine-1,3-dione and 9-acetyl-2-methyl-9H-benzo[b]pyrrolo[3,4-e][1,4]thiazine-1,3-dione, have been disclosed in Nippon Kagaku Kaishi (1992), (11), 1392-6 and Zeitschrift fuer Chemie (1987), 27(6), 211-12.

Therefore, according to a second aspect, the invention also provides novel compounds of formula I having good fungicidal activity against phytopathogenic harmful fungi:

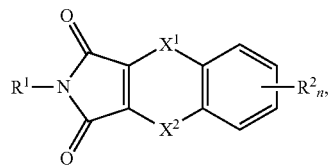

wherein:
X$^1$ is S, S=O, O or NR;
X$^2$ is S, O or NR;
R is hydrogen, NR$^A$R$^B$, OH, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio, $C_3$-$C_6$-cycloalkyl, $C_3$-$C_6$-cycloalkenyl, $C_3$-$C_6$-cycloalkyl-$C_1$-$C_6$-alkyl, $C_2$-$C_6$-alkenyl, $C_1$-$C_6$-alkylcarbonyl or phenyl;
R$^A$, R$^B$ independently of one another are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_6$-alkylcarbonyl, $C_1$-$C_6$-alkenylcarbonyl, $C_1$-$C_6$-alkynylcarbonyl, $C_1$-$C_6$-alkoxycarbonyl, $C_1$-$C_6$-alkenyloxycarbonyl, $C_1$-$C_6$-alkynyloxycarbonyl, $C_1$-$C_6$-alkylaminocarbonyl, di($C_1$-$C_6$-alkyl)aminocarbonyl, $C_1$-$C_6$-alkenylaminocarbonyl or $C_1$-$C_6$-alkynylaminocarbonyl;
R$^1$ is hydrogen, OH, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio, $C_3$-$C_6$-cycloalkyl, $C_3$-$C_6$-cycloalkenyl, $C_3$-$C_6$-cycloalkyl-$C_1$-$C_6$-alkyl, $C_2$-$C_6$-alkenyl or $C_1$-$C_6$-alkylcarbonyl;
R$^2$ is halogen, OH, CN, nitro, $C_1$-$C_6$-alkyl, $C_1$-$C_6$-alkoxy, $C_3$-$C_6$-cycloalkyl, $C_3$-$C_6$-cycloalkenyl, $C_3$-$C_6$-cycloalkyl-$C_1$-$C_6$-alkyl, $C_2$-$C_6$-alkenyl, $C_2$-$C_6$-alkynyl, $C_1$-$C_6$-alkylcarbonyl, $C_1$-$C_6$-alkenylcarbonyl, $C_1$-$C_6$-alkynylcarbonyl, $C_1$-$C_6$-alkoxycarbonyl, $C_1$-$C_6$-alkenyloxycarbonyl, $C_1$-$C_6$-alkynyloxycarbonyl, $C_1$-$C_6$-alkylaminocarbonyl, di($C_1$-$C_6$-alkyl)aminocarbonyl, $C_1$-$C_6$-alkenylaminocarbonyl or $C_1$-$C_6$-alkynylaminocarbonyl or phenyl;
n is an integer between 0 and 4,
wherein the aliphatic and cyclic groups R, R$^1$ and R$^2$ may carry 1, 2, 3, 4 or up to the maximum possible number of identical or different groups R$^a$:
R$^a$ is amino, halogen, hydroxyl, nitro, CN, carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_8$-cycloalkenyl, $C_1$-$C_6$-alkylamino, $C_1$-$C_4$-alkylcarbonyl, $C_1$-$C_4$-alkoxycarbonyl, $C_1$-$C_4$-alkylcarbonyloxy or NR$^A$R$^B$;
and the N-oxides and the agriculturally acceptable salts of the compounds of formula I,
except for 4-acetyl-4,9-dihydro-pyrrolo[3,4-b]quinoxaline-1,3-dione, 2,4-diacetyl-4,9-dihydro-pyrrolo[3,4-b]quinoxaline-1,3-dione, 2,4,9-triacetyl-4,9-dihydro-pyrrolo[3,4-b]quinoxaline-1,3-dione, 2-methyl-9H-benzo[b]pyrrolo[3,4-e][1,4]thiazine-1,3-dione and 9-acetyl-2-methyl-9H-benzo[b]pyrrolo[3,4-e][1,4]thiazine-1,3-dione.

The term "compounds I" refers to compounds of formula I. Likewise, this terminology applies to all sub-formulae, e.g. "compounds I.A" refers to compounds of formula I.A or "compounds V" refers to compounds of formula V, etc.

The compounds I can be by various routes in analogy to prior art processes known per se for preparing (cf. Tetrahedron Lett. 49, (1969), 4273-4274) and, advantageously, by the synthesis shown in the following schemes and in the experimental part of this application.

In a first step, for example (cf. Synthetic Commun. 36, (2006), 3591-3597; Revue Roumaine de Chimie 50, (2005), 601-607; Chem. Ind. London 4, (1991), 130; JP 571200502; DD 218261; DD 224031), dichloromaleic anhydride II is reacted, in a first step, with an amine III, if appropriate in the presence of a diluent to obtain maleic imides IV:

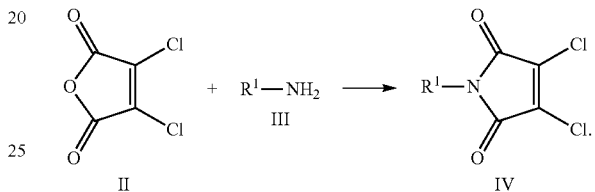

Thereafter, for example (cf. Tetrahedron Lett. 26(15), 2689 (1995); Tetrahedron Lett. 55(40), 11859 (1999); European Polym. J. 24(3), 255-258, (1988)) the resulting maleic imides IV are then reacted with benzene-1,2-diols, dithiols or diamines of formula V, preferably in the presence of a base (e.g. KOH, NaOH or $K_2CO_3$) and diluent, to obtain compounds I:

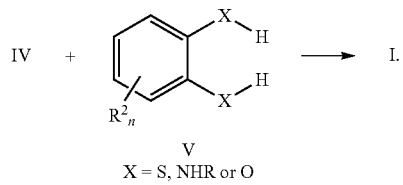

X = S, NHR or O

If appropriate, the resulting compounds I can subsequently be oxidized e.g. with nitric acid to form compounds I, wherein X is S=O. If individual compounds I cannot be obtained by the routes described above, they can be prepared by derivatization of other compounds I.

The N-oxides may be prepared from the compounds I according to conventional oxidation methods, e.g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during workup for use or during application (e.g. under the action of light, acids or bases). Such conversions may also take place after use, e.g. in the treatment of plants in the treated plant, or in the harmful fungus to be controlled.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_1$-$C_4$-alkyl" refers to a straight-chained or branched alkyl group having 1 to 4 carbon atoms.

The term "$C_1$-$C_6$-alkoxy" refers to a straight-chain or branched alkyl group having 1 to 4 carbon atoms which is bonded via an oxygen, at any position in the alkyl group, e.g. $OCH_3$, $OCH_2CH_3$, $O(CH_2)_2CH_3$, 1-methylethoxy, $O(CH_2)_3CH_3$, 1-methylpropoxy, 2-methylpropoxy or 1,1-dimethylethoxy, $O(CH_2)_4CH_3$ or $O(CH_2)_5CH_3$. Likewise, the term "$C_1$-$C_4$-alkoxy" refers to a straight-chain or branched alkyl group having 1 to 4 carbon atoms which is bonded via an oxygen, at any position in the alkyl group.

The term "$C_1$-$C_4$-alkylamino" refers to an amino radical carrying one $C_1$-$C_4$-alkyl group as substituent, e.g. methylamino, ethylamino, propylamino, 1-methylethylamino, butylamino, 1-methylpropylamino, 2-methylpropylamino, 1,1-dimethylethylamino and the like. Likewise, the term "$C_1$-$C_6$-alkylamino" refers to an amino radical carrying one $C_1$-$C_6$-alkyl group as substituent.

The term "di($C_1$-$C_4$-alkyl)amino" refers to an amino radical carrying two identical or different $C_1$-$C_4$-alkyl groups as substituents, e.g. dimethylamino, diethylamino, di-n-propylamino, diisopropylamino, N-ethyl-N-methylamino, N-(n-propyl)-N-methylamino, N-(isopropyl)-N methylamino, N-(n-butyl)-N-methylamino, N-(n-pentyl)-N-methylamino, N-(2-butyl)-N methylamino, N-(isobutyl)-N-methylamino, and the like. Likewise, the term "di($C_1$-$C_6$-alkyl)amino" refers to an amino radical carrying two identical or different $C_1$-$C_6$-alkyl groups as substituents.

The term "$C_1$-$C_4$-alkylcarbonyl" refers to a $C_1$-$C_6$-alkyl radical which is attached via a carbonyl group. The term "($C_1$-$C_6$-alkoxy)carbonyl" refers to a $C_1$-$C_6$-alkoxy radical which is attached via a carbonyl group.

The term "$C_1$-$C_6$-alkylaminocarbonyl" refers to a $C_1$-$C_6$-alkylamino radical which is attached via a carbonyl group. Likewise, the term "di($C_1$-$C_6$-alkyl)aminocarbonyl" refers to a di($C_1$-$C_6$)alkylamino radical which is attached via a carbonyl group.

The term "$C_2$-$C_4$-alkenyl" refers to a straight-chain or branched unsaturated hydrocarbon radical having 2 to 4 carbon atoms and a double bond in any position, e.g. ethenyl, 1-propenyl, 2-propenyl(allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. Likewise, the term "$C_2$-$C_6$-alkenyl" refers to a straight-chain or branched unsaturated hydrocarbon radical having 2 to 6 carbon atoms and a double bond in any position.

The term "$C_2$-$C_4$-alkynyl" refers to a straight-chain or branched unsaturated hydrocarbon radical having 2 to 4 carbon atoms and containing at least one triple bond, such as ethynyl, 1-propynyl, 2-propynyl, 1-butynyl, 2-butynyl, 3-butynyl, 1-methyl-2-propynyl. Likewise, the term "$C_2$-$C_6$-alkynyl" refers to a straight-chain or branched unsaturated hydrocarbon radical having 2 to 6 carbon atoms and at least one triple bond.

The term "$C_3$-$C_6$-cycloalkyl" refers to monocyclic, bicyclic, saturated hydrocarbon radicals having 3 to 6 carbon ring members, such as cyclopropyl, cyclobutyl, cyclopentyl or cyclohexyl.

Likewise, the term "$C_3$-$C_6$-cycloalkenyl" refers to unsaturated hydrocarbon radicals having 3 to 6 carbon ring members and a double bond in any position, such as cyclopropenyl, cyclobutenyl, cyclopentenyl or cyclohexenyl.

The term "$C_3$-$C_6$-cycloalkyl-$C_1$-$C_6$-alkyl" refers to alkyl having 1 to 6 carbon atoms (as defined above), wherein one hydrogen atom of the alkyl radical is replaced by a cycloalkyl radical having 3 to 6 carbon atoms (as defined above).

Agriculturally acceptable salts of compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

The compounds of formula I can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In respect of the variables, the embodiments of the intermediates correspond to the embodiments of the compounds I.

Preference is given to those compounds I and where applicable also to compounds of all sub-formulae provided herein, e.g. formulae I.A, I.B to I.G and to the intermediates such as compounds II, III, IV and V, wherein the substituents and variables (such as n, $X^1$, $X^2$, R, $R^1$, $R^2$, $R^A$, $R^B$ and $R^a$) have independently of each other or more preferably in combination the following meanings:

One embodiment of the invention relates to compounds I, wherein $X^1$ and $X^2$ are S and wherein $R^{2a}$ to $R^{2d}$ have one of the definitions of $R^2$ or are hydrogen, which are of formula I.A

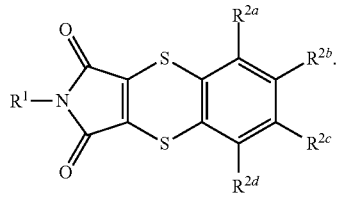

I.A

Another embodiment relates to compounds I, wherein $X^1$ is S=O and $X^2$ is S and wherein $R^{2a}$ to $R^{2d}$ have one of the definitions of $R^2$ or are hydrogen, which are of formula I.B

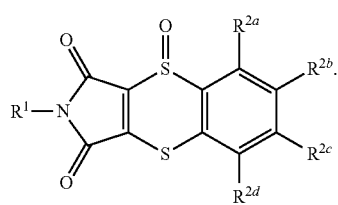

I.B

A further embodiment relates to compounds I, wherein $X^1$ and $X^2$ are O and wherein $R^{2a}$ to $R^{2d}$ have one of the definitions of $R^2$ or are hydrogen, which are of formula I.C

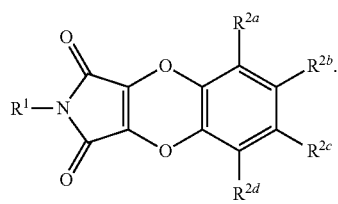

I.C

A further embodiment relates to compounds I, wherein $X^1$ and $X^2$ are NH and wherein $R^{2a}$ to $R^{2d}$ have one of the definitions of $R^2$ or are hydrogen, which are of formula I.D

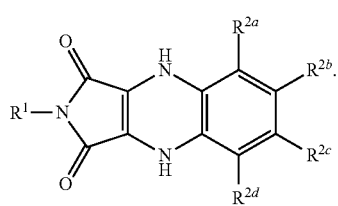

I.D

A further embodiment relates to compounds I, wherein $X^1$ and $X^2$ are $NCH_3$ and wherein $R^{2a}$ to $R^{2d}$ have one of the definitions of $R^2$ or are hydrogen, which are of formula I.E

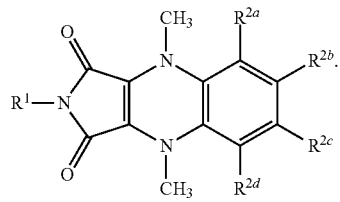

I.E

A further embodiment relates to compounds I, wherein $X^1$ and $X^2$ are $N(CO)CH_3$ and wherein $R^{2a}$ to $R^{2d}$ have one of the definitions of $R^2$ or are hydrogen, which are of formula I.F

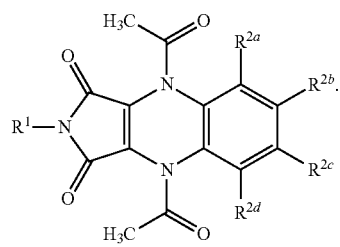

I.F

A further embodiment relates to compounds I, wherein $X^1$ is S and $X^2$ is NH and wherein $R^{2a}$ to $R^{2d}$ have one of the definitions of $R^2$ or are hydrogen, which are of formula I.G

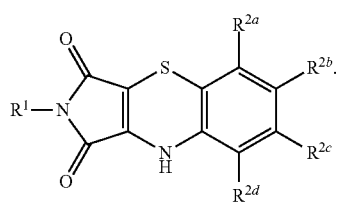

I.G

A further embodiment relates to compounds I, wherein $X^1$ and $X^2$ are identical.

A further embodiment relates to compounds I, wherein $X^1$ and $X^2$ together cannot be NR and S (to exclude combinations $X^1$=NR, $X^2$=S and $X^1$=S, $X^2$=NR).

A further embodiment relates to compounds I, wherein $X^1$ and $X^2$ cannot be NH and S (to exclude combinations $X^1$=NH, $X^2$=S and $X^1$=S, $X^2$=NH).

A further embodiment relates to compounds I, wherein $X^1$ and $X^2$ cannot be NH and O (to exclude combinations $X^1$=NH, $X^2$=O and $X^1$=O, $X^2$=NH).

In one embodiment, $R^1$ is selected from hydrogen, $C_1$-$C_6$-alkyl and $C_1$-$C_6$-alkoxy, more preferably selected from hydrogen, methyl, ethyl, methoxy and ethoxy, even more preferably from hydrogen and methyl.

In a further embodiment, n is preferably selected from 0, 1 and 2; even more preferably from 0 and 1, in particular 1. Whenever n is 1, $R^2$ is preferably in position of $R^{2b}$ or $R^{2c}$ as depicted in formulae I.A to I.C. Whenever n is 1, $R^2$ is preferably identical to $R^1$.

In a further embodiment, n is 0.

In a further embodiment, $R^2$ is selected from hydrogen, halogen, CN, nitro, $C_1$-$C_6$-alkyl and $C_1$-$C_6$-halogenalkyl, more preferably selected from hydrogen, methyl, CN and nitro and even more preferably from hydrogen and methyl.

In a further embodiment, $R^2$ is substituted by 1 to 3 halogen, preferably selected from Cl and F.

In a further embodiment, $R^2$ is $CF_3$.

A skilled person will readily understand that the preferences given in connection with compounds I apply for formulae I.A, I.B, I.C, I.D, I.E and I.F as defined above.

With respect to their use, particular preference is given to the 20480 compounds of formulae I.A, I.B, IC. I.D, I.E, I.F and I.G compiled in the tables 1 to 32 below. Here, the groups mentioned in the Tables for a substituent are furthermore, independently of the combination wherein they are mentioned, a particularly preferred embodiment of the substituent in question.

Table 1: Compounds I to 640 of formula I.A, wherein $R^1$ is hydrogen and the meaning of $R^{2a}$, $R^{2b}$, $R^{2c}$ and $R^{2d}$ for each compound corresponds to one line of table A.

Table 2: Compounds 641 to 1280 of formula I.A, wherein $R^1$ is methyl and the meaning of $R^{2a}$, $R^{2b}$, $R^{2c}$ and $R^{2d}$ for each compound corresponds to one line of table A.

Table 3: Compounds 1281 to 1920 of formula I.A, wherein $R^1$ is ethyl and the meaning of $R^{2a}$, $R^{2b}$, $R^{2c}$ and $R^{2d}$ for each compound corresponds to one line of table A.

Table 4: Compounds 1921 to 2560 of formula I.A, wherein $R^1$ is methoxy and the meaning of $R^{2a}$, $R^{2b}$, $R^{2c}$ and $R^{2d}$ for each compound corresponds to one line of table A.

Tables 5 to 8: Compounds 2561 to 5120 of formula I.B, wherein $R^1$ is defined as in Tables 1 to 4, and the meaning of $R^{2a}$, $R^{2b}$, $R^{2c}$ and $R^{2d}$ for each compound corresponds to one line of table A.

Tables 9 to 12: Compounds 5121 to 7680 of formula I.B, wherein $R^1$ is defined as in Tables 1 to 4, and the meaning of $R^{2a}$, $R^{2b}$, $R^{2c}$ and $R^{2d}$ for each compound corresponds to one line of table A.

Tables 13 to 16: Compounds 7681 to 10240 of formula I.C, wherein $R^1$ is defined as in Tables 1 to 4, and the meaning of $R^{2a}$, $R^{2b}$, $R^{2c}$ and $R^{2d}$ for each compound corresponds to one line of table A.

Tables 17 to 20: Compounds 10241 to 12800 of formula I.D, wherein $R^1$ is defined as in Tables 1 to 4, and the meaning of $R^{2a}$, $R^{2b}$, $R^{2c}$ and $R^{2d}$ for each compound corresponds to one line of table A.

Tables 21 to 24: Compounds 12801 to 15360 of formula I.E, wherein $R^1$ is defined as in Tables 1 to 4, and the meaning of $R^{2a}$, $R^{2b}$, $R^{2c}$ and $R^{2d}$ for each compound corresponds to one line of table A.

Tables 25 to 28: Compounds 15361 to 17920 of formula I.F, wherein $R^1$ is defined as in Tables 1 to 4, and the meaning of $R^{2a}$, $R^{2b}$, $R^{2c}$ and $R^{2d}$ for each compound corresponds to one line of table A.

Tables 29 to 32: Compounds 17921 to 20480 of formula I.G, wherein $R^1$ is defined as in Tables 1 to 4, and the meaning of $R^{2a}$, $R^{2b}$, $R^{2c}$ and $R^{2d}$ for each compound corresponds to one line of table A.

TABLE A

| line | $R^{2a}$ | $R^{2b}$ | $R^{2c}$ | $R^{2d}$ |
|---|---|---|---|---|
| 1 | H | H | H | H |
| 2 | F | H | H | H |
| 3 | Cl | H | H | H |
| 4 | Br | H | H | H |
| 5 | $CH_3$ | H | H | H |
| 6 | $CF_3$ | H | H | H |
| 7 | CN | H | H | H |
| 8 | $OCH_3$ | H | H | H |
| 9 | $OC_2H_5$ | H | H | H |
| 10 | $OCF_3$ | H | H | H |
| 11 | $OCHF_2$ | H | H | H |
| 12 | H | F | H | H |
| 13 | H | Cl | H | H |
| 14 | H | Br | H | H |
| 15 | H | $CH_3$ | H | H |
| 16 | H | $CF_3$ | H | H |
| 17 | H | CN | H | H |
| 18 | H | $OCH_3$ | H | H |
| 19 | H | $OC_2H_5$ | H | H |
| 20 | H | $OCF_3$ | H | H |
| 21 | H | $OCHF_2$ | H | H |
| 22 | H | H | F | H |
| 23 | H | H | Cl | H |
| 24 | H | H | Br | H |
| 25 | H | H | $CH_3$ | H |
| 26 | H | H | $CF_3$ | H |
| 27 | H | H | CN | H |
| 28 | H | H | $OCH_3$ | H |
| 29 | H | H | $OC_2H_5$ | H |
| 30 | H | H | $OCF_3$ | H |
| 31 | H | H | $OCHF_2$ | H |
| 32 | H | H | H | Cl |
| 33 | H | H | H | Br |
| 34 | H | H | H | $CH_3$ |
| 35 | H | H | H | $CF_3$ |
| 36 | H | H | H | CN |
| 37 | H | H | H | $OCH_3$ |
| 38 | H | H | H | $OC_2H_5$ |
| 39 | H | H | H | $OCF_3$ |
| 40 | H | H | H | $OCHF_2$ |
| 41 | F | F | H | H |
| 42 | Cl | F | H | H |
| 43 | Br | F | H | H |
| 44 | $CH_3$ | F | H | H |
| 45 | $CF_3$ | F | H | H |
| 46 | CN | F | H | H |
| 47 | $OCH_3$ | F | H | H |
| 48 | $OC_2H_5$ | F | H | H |
| 49 | $OCF_3$ | F | H | H |
| 50 | $OCHF_2$ | F | H | H |
| 51 | F | Cl | H | H |
| 52 | Cl | Cl | H | H |
| 53 | Br | Cl | H | H |
| 54 | $CH_3$ | Cl | H | H |
| 55 | $CF_3$ | Cl | H | H |
| 56 | CN | Cl | H | H |
| 57 | $OCH_3$ | Cl | H | H |
| 58 | $OC_2H_5$ | Cl | H | H |
| 59 | $OCF_3$ | Cl | H | H |
| 60 | $OCHF_2$ | Cl | H | H |
| 61 | F | Br | H | H |
| 62 | Cl | Br | H | H |
| 63 | Br | Br | H | H |
| 64 | $CH_3$ | Br | H | H |
| 65 | $CF_3$ | Br | H | H |
| 66 | CN | Br | H | H |
| 67 | $OCH_3$ | Br | H | H |
| 68 | $OC_2H_5$ | Br | H | H |
| 69 | $OCF_3$ | Br | H | H |
| 70 | $OCHF_2$ | Br | H | H |
| 71 | F | $CH_3$ | H | H |
| 72 | Cl | $CH_3$ | H | H |
| 73 | Br | $CH_3$ | H | H |
| 74 | $CH_3$ | $CH_3$ | H | H |
| 75 | $CF_3$ | $CH_3$ | H | H |
| 76 | CN | $CH_3$ | H | H |
| 77 | $OCH_3$ | $CH_3$ | H | H |
| 78 | $OC_2H_5$ | $CH_3$ | H | H |
| 79 | $OCF_3$ | $CH_3$ | H | H |
| 80 | $OCHF_2$ | $CH_3$ | H | H |
| 81 | F | $CF_3$ | H | H |
| 82 | Cl | $CF_3$ | H | H |
| 83 | Br | $CF_3$ | H | H |
| 84 | $CH_3$ | $CF_3$ | H | H |
| 85 | $CF_3$ | $CF_3$ | H | H |
| 86 | CN | $CF_3$ | H | H |
| 87 | $OCH_3$ | $CF_3$ | H | H |
| 88 | $OC_2H_5$ | $CF_3$ | H | H |

TABLE A-continued

| line | $R^{2a}$ | $R^{2b}$ | $R^{2c}$ | $R^{2d}$ |
|---|---|---|---|---|
| 89 | OCF$_3$ | CF$_3$ | H | H |
| 90 | OCHF$_2$ | CF$_3$ | H | H |
| 91 | F | CN | H | H |
| 92 | Cl | CN | H | H |
| 93 | Br | CN | H | H |
| 94 | CH$_3$ | CN | H | H |
| 95 | CF$_3$ | CN | H | H |
| 96 | CN | CN | H | H |
| 97 | OCH$_3$ | CN | H | H |
| 98 | OC$_2$H$_5$ | CN | H | H |
| 99 | OCF$_3$ | CN | H | H |
| 100 | OCHF$_2$ | CN | H | H |
| 101 | F | OCH$_3$ | H | H |
| 102 | Cl | OCH$_3$ | H | H |
| 103 | Br | OCH$_3$ | H | H |
| 104 | CH$_3$ | OCH$_3$ | H | H |
| 105 | CF$_3$ | OCH$_3$ | H | H |
| 106 | CN | OCH$_3$ | H | H |
| 107 | OCH$_3$ | OCH$_3$ | H | H |
| 108 | OC$_2$H$_5$ | OCH$_3$ | H | H |
| 109 | OCF$_3$ | OCH$_3$ | H | H |
| 110 | OCHF$_2$ | OCH$_3$ | H | H |
| 111 | F | OC$_2$H$_5$ | H | H |
| 112 | Cl | OC$_2$H$_5$ | H | H |
| 113 | Br | OC$_2$H$_5$ | H | H |
| 114 | CH$_3$ | OC$_2$H$_5$ | H | H |
| 115 | CF$_3$ | OC$_2$H$_5$ | H | H |
| 116 | CN | OC$_2$H$_5$ | H | H |
| 117 | OCH$_3$ | OC$_2$H$_5$ | H | H |
| 118 | OC$_2$H$_5$ | OC$_2$H$_5$ | H | H |
| 119 | OCF$_3$ | OC$_2$H$_5$ | H | H |
| 120 | OCHF$_2$ | OC$_2$H$_5$ | H | H |
| 121 | F | OCF$_3$ | H | H |
| 122 | Cl | OCF$_3$ | H | H |
| 123 | Br | OCF$_3$ | H | H |
| 124 | CH$_3$ | OCF$_3$ | H | H |
| 125 | CF$_3$ | OCF$_3$ | H | H |
| 126 | CN | OCF$_3$ | H | H |
| 127 | OCH$_3$ | OCF$_3$ | H | H |
| 128 | OC$_2$H$_5$ | OCF$_3$ | H | H |
| 129 | OCF$_3$ | OCF$_3$ | H | H |
| 130 | OCHF$_2$ | OCF$_3$ | H | H |
| 131 | F | OCHF$_2$ | H | H |
| 132 | Cl | OCHF$_2$ | H | H |
| 133 | Br | OCHF$_2$ | H | H |
| 134 | CH$_3$ | OCHF$_2$ | H | H |
| 135 | CF$_3$ | OCHF$_2$ | H | H |
| 136 | CN | OCHF$_2$ | H | H |
| 137 | OCH$_3$ | OCHF$_2$ | H | H |
| 138 | OC$_2$H$_5$ | OCHF$_2$ | H | H |
| 139 | OCF$_3$ | OCHF$_2$ | H | H |
| 140 | OCHF$_2$ | OCHF$_2$ | H | H |
| 141 | F | H | F | H |
| 142 | Cl | H | F | H |
| 143 | Br | H | F | H |
| 144 | CH$_3$ | H | F | H |
| 145 | CF$_3$ | H | F | H |
| 146 | CN | H | F | H |
| 147 | OCH$_3$ | H | F | H |
| 148 | OC$_2$H$_5$ | H | F | H |
| 149 | OCF$_3$ | H | F | H |
| 150 | OCHF$_2$ | H | F | H |
| 151 | F | H | Cl | H |
| 152 | Cl | H | Cl | H |
| 153 | Br | H | Cl | H |
| 154 | CH$_3$ | H | Cl | H |
| 155 | CF$_3$ | H | Cl | H |
| 156 | CN | H | Cl | H |
| 157 | OCH$_3$ | H | Cl | H |
| 158 | OC$_2$H$_5$ | H | Cl | H |
| 159 | OCF$_3$ | H | Cl | H |
| 160 | OCHF$_2$ | H | Cl | H |
| 161 | F | H | Br | H |
| 162 | Cl | H | Br | H |
| 163 | Br | H | Br | H |
| 164 | CH$_3$ | H | Br | H |
| 165 | CF$_3$ | H | Br | H |
| 166 | CN | H | Br | H |
| 167 | OCH$_3$ | H | Br | H |
| 168 | OC$_2$H$_5$ | H | Br | H |
| 169 | OCF$_3$ | H | Br | H |
| 170 | OCHF$_2$ | H | Br | H |
| 171 | F | H | CH$_3$ | H |
| 172 | Cl | H | CH$_3$ | H |
| 173 | Br | H | CH$_3$ | H |
| 174 | CH$_3$ | H | CH$_3$ | H |
| 175 | CF$_3$ | H | CH$_3$ | H |
| 176 | CN | H | CH$_3$ | H |
| 177 | OCH$_3$ | H | CH$_3$ | H |
| 178 | OC$_2$H$_5$ | H | CH$_3$ | H |
| 179 | OCF$_3$ | H | CH$_3$ | H |
| 180 | OCHF$_2$ | H | CH$_3$ | H |
| 181 | F | H | CF$_3$ | H |
| 182 | Cl | H | CF$_3$ | H |
| 183 | Br | H | CF$_3$ | H |
| 184 | CH$_3$ | H | CF$_3$ | H |
| 185 | CF$_3$ | H | CF$_3$ | H |
| 186 | CN | H | CF$_3$ | H |
| 187 | OCH$_3$ | H | CF$_3$ | H |
| 188 | OC$_2$H$_5$ | H | CF$_3$ | H |
| 189 | OCF$_3$ | H | CF$_3$ | H |
| 190 | OCHF$_2$ | H | CF$_3$ | H |
| 191 | F | H | CN | H |
| 192 | Cl | H | CN | H |
| 193 | Br | H | CN | H |
| 194 | CH$_3$ | H | CN | H |
| 195 | CF$_3$ | H | CN | H |
| 196 | CN | H | CN | H |
| 197 | OCH$_3$ | H | CN | H |
| 198 | OC$_2$H$_5$ | H | CN | H |
| 199 | OCF$_3$ | H | CN | H |
| 200 | OCHF$_2$ | H | CN | H |
| 201 | F | H | OCH$_3$ | H |
| 202 | Cl | H | OCH$_3$ | H |
| 203 | Br | H | OCH$_3$ | H |
| 204 | CH$_3$ | H | OCH$_3$ | H |
| 205 | CF$_3$ | H | OCH$_3$ | H |
| 206 | CN | H | OCH$_3$ | H |
| 207 | OCH$_3$ | H | OCH$_3$ | H |
| 208 | OC$_2$H$_5$ | H | OCH$_3$ | H |
| 209 | OCF$_3$ | H | OCH$_3$ | H |
| 210 | OCHF$_2$ | H | OCH$_3$ | H |
| 211 | F | H | OC$_2$H$_5$ | H |
| 212 | Cl | H | OC$_2$H$_5$ | H |
| 213 | Br | H | OC$_2$H$_5$ | H |
| 214 | CH$_3$ | H | OC$_2$H$_5$ | H |
| 215 | CF$_3$ | H | OC$_2$H$_5$ | H |
| 216 | CN | H | OC$_2$H$_5$ | H |
| 217 | OCH$_3$ | H | OC$_2$H$_5$ | H |
| 218 | OC$_2$H$_5$ | H | OC$_2$H$_5$ | H |
| 219 | OCF$_3$ | H | OC$_2$H$_5$ | H |
| 220 | OCHF$_2$ | H | OC$_2$H$_5$ | H |
| 221 | F | H | OCF$_3$ | H |
| 222 | Cl | H | OCF$_3$ | H |
| 223 | Br | H | OCF$_3$ | H |
| 224 | CH$_3$ | H | OCF$_3$ | H |
| 225 | CF$_3$ | H | OCF$_3$ | H |
| 226 | CN | H | OCF$_3$ | H |
| 227 | OCH$_3$ | H | OCF$_3$ | H |
| 228 | OC$_2$H$_5$ | H | OCF$_3$ | H |
| 229 | OCF$_3$ | H | OCF$_3$ | H |
| 230 | OCHF$_2$ | H | OCF$_3$ | H |
| 231 | F | H | OCHF$_2$ | H |
| 232 | Cl | H | OCHF$_2$ | H |
| 233 | Br | H | OCHF$_2$ | H |
| 234 | CH$_3$ | H | OCHF$_2$ | H |
| 235 | CF$_3$ | H | OCHF$_2$ | H |
| 236 | CN | H | OCHF$_2$ | H |
| 237 | OCH$_3$ | H | OCHF$_2$ | H |
| 238 | OC$_2$H$_5$ | H | OCHF$_2$ | H |
| 239 | OCF$_3$ | H | OCHF$_2$ | H |
| 240 | OCHF$_2$ | H | OCHF$_2$ | H |
| 241 | F | H | H | F |
| 242 | Cl | H | H | F |
| 243 | Br | H | H | F |
| 244 | CH$_3$ | H | H | F |

TABLE A-continued

| line | $R^{2a}$ | $R^{2b}$ | $R^{2c}$ | $R^{2d}$ |
|---|---|---|---|---|
| 245 | $CF_3$ | H | H | F |
| 246 | CN | H | H | F |
| 247 | $OCH_3$ | H | H | F |
| 248 | $OC_2H_5$ | H | H | F |
| 249 | $OCF_3$ | H | H | F |
| 250 | $OCHF_2$ | H | H | F |
| 251 | F | H | H | Cl |
| 252 | Cl | H | H | Cl |
| 253 | Br | H | H | Cl |
| 254 | $CH_3$ | H | H | Cl |
| 255 | $CF_3$ | H | H | Cl |
| 256 | CN | H | H | Cl |
| 257 | $OCH_3$ | H | H | Cl |
| 258 | $OC_2H_5$ | H | H | Cl |
| 259 | $OCF_3$ | H | H | Cl |
| 260 | $OCHF_2$ | H | H | Cl |
| 261 | F | H | H | Br |
| 262 | Cl | H | H | Br |
| 263 | Br | H | H | Br |
| 264 | $CH_3$ | H | H | Br |
| 265 | $CF_3$ | H | H | Br |
| 266 | CN | H | H | Br |
| 267 | $OCH_3$ | H | H | Br |
| 268 | $OC_2H_5$ | H | H | Br |
| 269 | $OCF_3$ | H | H | Br |
| 270 | $OCHF_2$ | H | H | Br |
| 271 | F | H | H | $CH_3$ |
| 272 | Cl | H | H | $CH_3$ |
| 273 | Br | H | H | $CH_3$ |
| 274 | $CH_3$ | H | H | $CH_3$ |
| 275 | $CF_3$ | H | H | $CH_3$ |
| 276 | CN | H | H | $CH_3$ |
| 277 | $OCH_3$ | H | H | $CH_3$ |
| 278 | $OC_2H_5$ | H | H | $CH_3$ |
| 279 | $OCF_3$ | H | H | $CH_3$ |
| 280 | $OCHF_2$ | H | H | $CH_3$ |
| 281 | F | H | H | $CF_3$ |
| 282 | Cl | H | H | $CF_3$ |
| 283 | Br | H | H | $CF_3$ |
| 284 | $CH_3$ | H | H | $CF_3$ |
| 285 | $CF_3$ | H | H | $CF_3$ |
| 286 | CN | H | H | $CF_3$ |
| 287 | $OCH_3$ | H | H | $CF_3$ |
| 288 | $OC_2H_5$ | H | H | $CF_3$ |
| 289 | $OCF_3$ | H | H | $CF_3$ |
| 290 | $OCHF_2$ | H | H | $CF_3$ |
| 291 | F | H | H | CN |
| 292 | Cl | H | H | CN |
| 293 | Br | H | H | CN |
| 294 | $CH_3$ | H | H | CN |
| 295 | $CF_3$ | H | H | CN |
| 296 | CN | H | H | CN |
| 297 | $OCH_3$ | H | H | CN |
| 298 | $OC_2H_5$ | H | H | CN |
| 299 | $OCF_3$ | H | H | CN |
| 300 | $OCHF_2$ | H | H | CN |
| 301 | F | H | H | $OCH_3$ |
| 302 | Cl | H | H | $OCH_3$ |
| 303 | Br | H | H | $OCH_3$ |
| 304 | $CH_3$ | H | H | $OCH_3$ |
| 305 | $CF_3$ | H | H | $OCH_3$ |
| 306 | CN | H | H | $OCH_3$ |
| 307 | $OCH_3$ | H | H | $OCH_3$ |
| 308 | $OC_2H_5$ | H | H | $OCH_3$ |
| 309 | $OCF_3$ | H | H | $OCH_3$ |
| 310 | $OCHF_2$ | H | H | $OCH_3$ |
| 311 | F | H | H | $OC_2H_5$ |
| 312 | Cl | H | H | $OC_2H_5$ |
| 313 | Br | H | H | $OC_2H_5$ |
| 314 | $CH_3$ | H | H | $OC_2H_5$ |
| 315 | $CF_3$ | H | H | $OC_2H_5$ |
| 316 | CN | H | H | $OC_2H_5$ |
| 317 | $OCH_3$ | H | H | $OC_2H_5$ |
| 318 | $OC_2H_5$ | H | H | $OC_2H_5$ |
| 319 | $OCF_3$ | H | H | $OC_2H_5$ |
| 320 | $OCHF_2$ | H | H | $OC_2H_5$ |
| 321 | F | H | H | $OCF_3$ |
| 322 | Cl | H | H | $OCF_3$ |
| 323 | Br | H | H | $OCF_3$ |
| 324 | $CH_3$ | H | H | $OCF_3$ |
| 325 | $CF_3$ | H | H | $OCF_3$ |
| 326 | CN | H | H | $OCF_3$ |
| 327 | $OCH_3$ | H | H | $OCF_3$ |
| 328 | $OC_2H_5$ | H | H | $OCF_3$ |
| 329 | $OCF_3$ | H | H | $OCF_3$ |
| 330 | $OCHF_2$ | H | H | $OCF_3$ |
| 331 | F | H | H | $OCHF_2$ |
| 332 | Cl | H | H | $OCHF_2$ |
| 333 | Br | H | H | $OCHF_2$ |
| 334 | $CH_3$ | H | H | $OCHF_2$ |
| 335 | $CF_3$ | H | H | $OCHF_2$ |
| 336 | CN | H | H | $OCHF_2$ |
| 337 | $OCH_3$ | H | H | $OCHF_2$ |
| 338 | $OC_2H_5$ | H | H | $OCHF_2$ |
| 339 | $OCF_3$ | H | H | $OCHF_2$ |
| 340 | $OCHF_2$ | H | H | $OCHF_2$ |
| 341 | H | F | F | H |
| 342 | H | Cl | F | H |
| 343 | H | Br | F | H |
| 344 | H | $CH_3$ | F | H |
| 345 | H | $CF_3$ | F | H |
| 346 | H | CN | F | H |
| 347 | H | $OCH_3$ | F | H |
| 348 | H | $OC_2H_5$ | F | H |
| 349 | H | $OCF_3$ | F | H |
| 350 | H | $OCHF_2$ | F | H |
| 351 | H | F | Cl | H |
| 352 | H | Cl | Cl | H |
| 353 | H | Br | Cl | H |
| 354 | H | $CH_3$ | Cl | H |
| 355 | H | $CF_3$ | Cl | H |
| 356 | H | CN | Cl | H |
| 357 | H | $OCH_3$ | Cl | H |
| 358 | H | $OC_2H_5$ | Cl | H |
| 359 | H | $OCF_3$ | Cl | H |
| 360 | H | $OCHF_2$ | Cl | H |
| 361 | H | F | Br | H |
| 362 | H | Cl | Br | H |
| 363 | H | Br | Br | H |
| 364 | H | $CH_3$ | Br | H |
| 365 | H | $CF_3$ | Br | H |
| 366 | H | CN | Br | H |
| 367 | H | $OCH_3$ | Br | H |
| 368 | H | $OC_2H_5$ | Br | H |
| 369 | H | $OCF_3$ | Br | H |
| 370 | H | $OCHF_2$ | Br | H |
| 371 | H | F | $CH_3$ | H |
| 372 | H | Cl | $CH_3$ | H |
| 373 | H | Br | $CH_3$ | H |
| 374 | H | $CH_3$ | $CH_3$ | H |
| 375 | H | $CF_3$ | $CH_3$ | H |
| 376 | H | CN | $CH_3$ | H |
| 377 | H | $OCH_3$ | $CH_3$ | H |
| 378 | H | $OC_2H_5$ | $CH_3$ | H |
| 379 | H | $OCF_3$ | $CH_3$ | H |
| 380 | H | $OCHF_2$ | $CH_3$ | H |
| 381 | H | F | $CF_3$ | H |
| 382 | H | Cl | $CF_3$ | H |
| 383 | H | Br | $CF_3$ | H |
| 384 | H | $CH_3$ | $CF_3$ | H |
| 385 | H | $CF_3$ | $CF_3$ | H |
| 386 | H | CN | $CF_3$ | H |
| 387 | H | $OCH_3$ | $CF_3$ | H |
| 388 | H | $OC_2H_5$ | $CF_3$ | H |
| 389 | H | $OCF_3$ | $CF_3$ | H |
| 390 | H | $OCHF_2$ | $CF_3$ | H |
| 391 | H | F | CN | H |
| 392 | H | Cl | CN | H |
| 393 | H | Br | CN | H |
| 394 | H | $CH_3$ | CN | H |
| 395 | H | $CF_3$ | CN | H |
| 396 | H | CN | CN | H |
| 397 | H | $OCH_3$ | CN | H |
| 398 | H | $OC_2H_5$ | CN | H |
| 399 | H | $OCF_3$ | CN | H |
| 400 | H | $OCHF_2$ | CN | H |

TABLE A-continued

| line | R²ᵃ | R²ᵇ | R²ᶜ | R²ᵈ |
|---|---|---|---|---|
| 401 | H | F | OCH₃ | H |
| 402 | H | Cl | OCH₃ | H |
| 403 | H | Br | OCH₃ | H |
| 404 | H | CH₃ | OCH₃ | H |
| 405 | H | CF₃ | OCH₃ | H |
| 406 | H | CN | OCH₃ | H |
| 407 | H | OCH₃ | OCH₃ | H |
| 408 | H | OC₂H₅ | OCH₃ | H |
| 409 | H | OCF₃ | OCH₃ | H |
| 410 | H | OCHF₂ | OCH₃ | H |
| 411 | H | F | OC₂H₅ | H |
| 412 | H | Cl | OC₂H₅ | H |
| 413 | H | Br | OC₂H₅ | H |
| 414 | H | CH₃ | OC₂H₅ | H |
| 415 | H | CF₃ | OC₂H₅ | H |
| 416 | H | CN | OC₂H₅ | H |
| 417 | H | OCH₃ | OC₂H₅ | H |
| 418 | H | OC₂H₅ | OC₂H₅ | H |
| 419 | H | OCF₃ | OC₂H₅ | H |
| 420 | H | OCHF₂ | OC₂H₅ | H |
| 421 | H | F | OCF₃ | H |
| 422 | H | Cl | OCF₃ | H |
| 423 | H | Br | OCF₃ | H |
| 424 | H | CH₃ | OCF₃ | H |
| 425 | H | CF₃ | OCF₃ | H |
| 426 | H | CN | OCF₃ | H |
| 427 | H | OCH₃ | OCF₃ | H |
| 428 | H | OC₂H₅ | OCF₃ | H |
| 429 | H | OCF₃ | OCF₃ | H |
| 430 | H | OCHF₂ | OCF₃ | H |
| 431 | H | F | OCHF₂ | H |
| 432 | H | Cl | OCHF₂ | H |
| 433 | H | Br | OCHF₂ | H |
| 434 | H | CH₃ | OCHF₂ | H |
| 435 | H | CF₃ | OCHF₂ | H |
| 436 | H | CN | OCHF₂ | H |
| 437 | H | OCH₃ | OCHF₂ | H |
| 438 | H | OC₂H₅ | OCHF₂ | H |
| 439 | H | OCF₃ | OCHF₂ | H |
| 440 | H | OCHF₂ | OCHF₂ | H |
| 441 | H | F | H | F |
| 442 | H | Cl | H | F |
| 443 | H | Br | H | F |
| 444 | H | CH₃ | H | F |
| 445 | H | CF₃ | H | F |
| 446 | H | CN | H | F |
| 447 | H | OCH₃ | H | F |
| 448 | H | OC₂H₅ | H | F |
| 449 | H | OCF₃ | H | F |
| 450 | H | OCHF₂ | H | F |
| 451 | H | F | H | Cl |
| 452 | H | Cl | H | Cl |
| 453 | H | Br | H | Cl |
| 454 | H | CH₃ | H | Cl |
| 455 | H | CF₃ | H | Cl |
| 456 | H | CN | H | Cl |
| 457 | H | OCH₃ | H | Cl |
| 458 | H | OC₂H₅ | H | Cl |
| 459 | H | OCF₃ | H | Cl |
| 460 | H | OCHF₂ | H | Cl |
| 461 | H | F | H | Br |
| 462 | H | Cl | H | Br |
| 463 | H | Br | H | Br |
| 464 | H | CH₃ | H | Br |
| 465 | H | CF₃ | H | Br |
| 466 | H | CN | H | Br |
| 467 | H | OCH₃ | H | Br |
| 468 | H | OC₂H₅ | H | Br |
| 469 | H | OCF₃ | H | Br |
| 470 | H | OCHF₂ | H | Br |
| 471 | H | F | H | CH₃ |
| 472 | H | Cl | H | CH₃ |
| 473 | H | Br | H | CH₃ |
| 474 | H | CH₃ | H | CH₃ |
| 475 | H | CF₃ | H | CH₃ |
| 476 | H | CN | H | CH₃ |
| 477 | H | OCH₃ | H | CH₃ |
| 478 | H | OC₂H₅ | H | CH₃ |
| 479 | H | OCF₃ | H | CH₃ |
| 480 | H | OCHF₂ | H | CH₃ |
| 481 | H | F | H | CF₃ |
| 482 | H | Cl | H | CF₃ |
| 483 | H | Br | H | CF₃ |
| 484 | H | CH₃ | H | CF₃ |
| 485 | H | CF₃ | H | CF₃ |
| 486 | H | CN | H | CF₃ |
| 487 | H | OCH₃ | H | CF₃ |
| 488 | H | OC₂H₅ | H | CF₃ |
| 489 | H | OCF₃ | H | CF₃ |
| 490 | H | OCHF₂ | H | CF₃ |
| 491 | H | F | H | CN |
| 492 | H | Cl | H | CN |
| 493 | H | Br | H | CN |
| 494 | H | CH₃ | H | CN |
| 495 | H | CF₃ | H | CN |
| 496 | H | CN | H | CN |
| 497 | H | OCH₃ | H | CN |
| 498 | H | OC₂H₅ | H | CN |
| 499 | H | OCF₃ | H | CN |
| 500 | H | OCHF₂ | H | CN |
| 501 | H | F | H | OCH₃ |
| 502 | H | Cl | H | OCH₃ |
| 503 | H | Br | H | OCH₃ |
| 504 | H | CH₃ | H | OCH₃ |
| 505 | H | CF₃ | H | OCH₃ |
| 506 | H | CN | H | OCH₃ |
| 507 | H | OCH₃ | H | OCH₃ |
| 508 | H | OC₂H₅ | H | OCH₃ |
| 509 | H | OCF₃ | H | OCH₃ |
| 510 | H | OCHF₂ | H | OCH₃ |
| 511 | H | F | H | OC₂H₅ |
| 512 | H | Cl | H | OC₂H₅ |
| 513 | H | Br | H | OC₂H₅ |
| 514 | H | CH₃ | H | OC₂H₅ |
| 515 | H | CF₃ | H | OC₂H₅ |
| 516 | H | CN | H | OC₂H₅ |
| 517 | H | OCH₃ | H | OC₂H₅ |
| 518 | H | OC₂H₅ | H | OC₂H₅ |
| 519 | H | OCF₃ | H | OC₂H₅ |
| 520 | H | OCHF₂ | H | OC₂H₅ |
| 521 | H | F | H | OCF₃ |
| 522 | H | Cl | H | OCF₃ |
| 523 | H | Br | H | OCF₃ |
| 524 | H | CH₃ | H | OCF₃ |
| 525 | H | CF₃ | H | OCF₃ |
| 526 | H | CN | H | OCF₃ |
| 527 | H | OCH₃ | H | OCF₃ |
| 528 | H | OC₂H₅ | H | OCF₃ |
| 529 | H | OCF₃ | H | OCF₃ |
| 530 | H | OCHF₂ | H | OCF₃ |
| 531 | H | F | H | OCHF₂ |
| 532 | H | Cl | H | OCHF₂ |
| 533 | H | Br | H | OCHF₂ |
| 534 | H | CH₃ | H | OCHF₂ |
| 535 | H | CF₃ | H | OCHF₂ |
| 536 | H | CN | H | OCHF₂ |
| 537 | H | OCH₃ | H | OCHF₂ |
| 538 | H | OC₂H₅ | H | OCHF₂ |
| 539 | H | OCF₃ | H | OCHF₂ |
| 540 | H | OCHF₂ | H | OCHF₂ |
| 541 | H | H | F | F |
| 542 | H | H | Cl | F |
| 543 | H | H | Br | F |
| 544 | H | H | CH₃ | F |
| 545 | H | H | CF₃ | F |
| 546 | H | H | CN | F |
| 547 | H | H | OCH₃ | F |
| 548 | H | H | OC₂H₅ | F |
| 549 | H | H | OCF₃ | F |
| 550 | H | H | OCHF₂ | F |
| 551 | H | H | F | Cl |
| 552 | H | H | Cl | Cl |
| 553 | H | H | Br | Cl |
| 554 | H | H | CH₃ | Cl |
| 555 | H | H | CF₃ | Cl |
| 556 | H | H | CN | Cl |

TABLE A-continued

| line | $R^{2a}$ | $R^{2b}$ | $R^{2c}$ | $R^{2d}$ |
|---|---|---|---|---|
| 557 | H | H | OCH$_3$ | Cl |
| 558 | H | H | OC$_2$H$_5$ | Cl |
| 559 | H | H | OCF$_3$ | Cl |
| 560 | H | H | OCHF$_2$ | Cl |
| 561 | H | H | F | Br |
| 562 | H | H | Cl | Br |
| 563 | H | H | Br | Br |
| 564 | H | H | CH$_3$ | Br |
| 565 | H | H | CF$_3$ | Br |
| 566 | H | H | CN | Br |
| 567 | H | H | OCH$_3$ | Br |
| 568 | H | H | OC$_2$H$_5$ | Br |
| 569 | H | H | OCF$_3$ | Br |
| 570 | H | H | OCHF$_2$ | Br |
| 571 | H | H | F | CH$_3$ |
| 572 | H | H | Cl | CH$_3$ |
| 573 | H | H | Br | CH$_3$ |
| 574 | H | H | CH$_3$ | CH$_3$ |
| 575 | H | H | CF$_3$ | CH$_3$ |
| 576 | H | H | CN | CH$_3$ |
| 577 | H | H | OCH$_3$ | CH$_3$ |
| 578 | H | H | OC$_2$H$_5$ | CH$_3$ |
| 579 | H | H | OCF$_3$ | CH$_3$ |
| 580 | H | H | OCHF$_2$ | CH$_3$ |
| 581 | H | H | F | CF$_3$ |
| 582 | H | H | Cl | CF$_3$ |
| 583 | H | H | Br | CF$_3$ |
| 584 | H | H | CH$_3$ | CF$_3$ |
| 585 | H | H | CF$_3$ | CF$_3$ |
| 586 | H | H | CN | CF$_3$ |
| 587 | H | H | OCH$_3$ | CF$_3$ |
| 588 | H | H | OC$_2$H$_5$ | CF$_3$ |
| 589 | H | H | OCF$_3$ | CF$_3$ |
| 590 | H | H | OCHF$_2$ | CF$_3$ |
| 591 | H | H | F | CN |
| 592 | H | H | Cl | CN |
| 593 | H | H | Br | CN |
| 594 | H | H | CH$_3$ | CN |
| 595 | H | H | CF$_3$ | CN |
| 596 | H | H | CN | CN |
| 597 | H | H | OCH$_3$ | CN |
| 598 | H | H | OC$_2$H$_5$ | CN |
| 599 | H | H | OCF$_3$ | CN |
| 600 | H | H | OCHF$_2$ | CN |
| 601 | H | H | F | OCH$_3$ |
| 602 | H | H | Cl | OCH$_3$ |
| 603 | H | H | Br | OCH$_3$ |
| 604 | H | H | CH$_3$ | OCH$_3$ |
| 605 | H | H | CF$_3$ | OCH$_3$ |
| 606 | H | H | CN | OCH$_3$ |
| 607 | H | H | OCH$_3$ | OCH$_3$ |
| 608 | H | H | OC$_2$H$_5$ | OCH$_3$ |
| 609 | H | H | OCF$_3$ | OCH$_3$ |
| 610 | H | H | OCHF$_2$ | OCH$_3$ |
| 611 | H | H | F | OC$_2$H$_5$ |
| 612 | H | H | Cl | OC$_2$H$_5$ |
| 613 | H | H | Br | OC$_2$H$_5$ |
| 614 | H | H | CH$_3$ | OC$_2$H$_5$ |
| 615 | H | H | CF$_3$ | OC$_2$H$_5$ |
| 616 | H | H | CN | OC$_2$H$_5$ |
| 617 | H | H | OCH$_3$ | OC$_2$H$_5$ |
| 618 | H | H | OC$_2$H$_5$ | OC$_2$H$_5$ |
| 619 | H | H | OCF$_3$ | OC$_2$H$_5$ |
| 620 | H | H | OCHF$_2$ | OC$_2$H$_5$ |
| 621 | H | H | F | OCF$_3$ |
| 622 | H | H | Cl | OCF$_3$ |
| 623 | H | H | Br | OCF$_3$ |
| 624 | H | H | CH$_3$ | OCF$_3$ |
| 625 | H | H | CF$_3$ | OCF$_3$ |
| 626 | H | H | CN | OCF$_3$ |
| 627 | H | H | OCH$_3$ | OCF$_3$ |
| 628 | H | H | OC$_2$H$_5$ | OCF$_3$ |
| 629 | H | H | OCF$_3$ | OCF$_3$ |
| 630 | H | H | OCHF$_2$ | OCF$_3$ |
| 631 | H | H | F | OCHF$_2$ |
| 632 | H | H | Cl | OCHF$_2$ |
| 633 | H | H | Br | OCHF$_2$ |
| 634 | H | H | CH$_3$ | OCHF$_2$ |
| 635 | H | H | CF$_3$ | OCHF$_2$ |
| 636 | H | H | CN | OCHF$_2$ |
| 637 | H | H | OCH$_3$ | OCHF$_2$ |
| 638 | H | H | OC$_2$H$_5$ | OCHF$_2$ |
| 639 | H | H | OCF$_3$ | OCHF$_2$ |
| 640 | H | H | OCHF$_2$ | OCHF$_2$ |

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://ceragmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted posttranslational modification of protein(s), oligo- or polypeptides e.g. by glycosylation or polymer additions such as prenylated, acetylated or farnesylated moieties or PEG moieties.

The compounds I and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Alternana* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. soljina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorodniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporiodes*); *Corticium* spp., e.g. *C. sasakii* (sheath blight) on rice; *Corynespora cassilcola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria lifiodendri*. Black Foot Disease) and ornamentals; *Dematophora* (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophllum* and/or *Botryosphaeria obtusa*; *Elsinoe* spp. on pome fruits (*E. pyre*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohlium* (syn. *Helminthosporium*) spp. on corn (e.g. *E. turcicum*); *Fusarium* (teleomorph: *berella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticilliodes* on corn; *Gaeumannomyces graminis* (take-all) on cereals (e.g. wheat or barley) and corn; *Gibberella* spp. on cereals (e.g. *G. zeae*) and rice (e.g. *G. fujikuroi*. Bakanae disease); *Glomerella cingulata* on vines, pome fruits and other plants and *G. gossypii* on cotton; Grainstaining complex on rice; *Guignardia bewellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphda* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P.* hordei (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyriculana* spp., e.g. *P. oryzae*(teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphandermatum*); *Ramularia* spp., e.g. *R. collo-cygni* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (Rhizoctonia spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici*(*Septoria* blotch) on wheat and *S*. (syn. *Stagonospora*) *nodorum* (*Stagonospora* blotch) on cereals; *Uncinula* (syn. *Erysiphe*) *necator*(powdery mildew, anamorph: *Odium tuckeri*) on vines; *Setospaena* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nulla* and *U. avaenae*), corn (e.g. *U. maydis*: corn smut) and sugar cane; *Ventura* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds I can be used, is intended to illustrate the possible combinations but does not limit them:

A) Respiration inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)phenyl)-2-methoxyimino-N-methyl-acetamide, pyribencarb, triclopyricarb/chlorodincarb, famoxadone, fenamidone;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl2-methylpropanoate inhibitors of complex II (e.g. carboxamides): benodanil, bixafen, boscalid, carboxin, fenfuram, fluopyram, flutolanil, fluxapyroxad, furametpyr, isopyrazam, mepronil, oxylcarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol biosynthesis inhibitors (SBI fungicides)

C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[Rel-(2S;3R)-3-(2-chlorophenyl)-2-(2,4-difluorophenyl)oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic acid synthesis inhibitors phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

D) Inhibitors of cell division and cytoskeleton tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of amino acid and protein synthesis methionine synthesis inhibitors (anilino-pyrimidines): cyprodinil, mepanipyrim, pyrimethanil;

protein synthesis inhibitors: blasticidin-S, kasugamycin, kasugamycin hydrochloridehydrate, mildiomycin, streptomycin, oxytetracyclin, polyoxine, validamycin A;

F) Signal transduction inhibitors

MAP/histidine kinase inhibitors: fluoroimid, iprodione, procymidone, vinclozolin, fenpiclonil, fludioxonil;

G protein inhibitors: quinoxyfen;

G) Lipid and membrane synthesis inhibitors
   Phospholipid biosynthesis inhibitors: edifenphos, iprobenfos, pyrazophos, isoprothiolane;
   lipid peroxidation: dicloran, quintozene, tecnazene, tolclofos-methyl, biphenyl, chloroneb, etridiazole;
   phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl)carbamic acid-(4-fluorophenyl)ester;
   compounds affecting cell membrane permeability and fatty acides: propamocarb, propamocarb-hydrochlorid
   fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone H) Inhibitors with Multi Site Action
   inorganic active substances: Bordeaux mixture, copper acetate, copper hydroxide, copper oxychloride, basic copper sulfate, sulfur;
   thio- and dithiocarbamates: ferbam, mancozeb, maneb, metam, metiram, propineb, thiram, zineb, ziram;
   organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
   guanidines and others: guanidine, dodine, dodine free base, guazatine, guazatineacetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)tetraone;

I) Cell wall synthesis inhibitors
   inhibitors of glucan synthesis: validamycin, polyoxin B;
   melanin synthesis inhibitors: pyroquilon, tricyclazole, carpropamid, dicyclomet, fenoxanil;

J) Plant defence inducers
   acibenzolar-5-methyl, probenazole, isotianil, tiadinil, prohexadione-calcium; phosphonates: fosetyl, fosetyl-aluminum, phosphorous acid and its salts;

K) Unknown mode of action
   bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluorophenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethylN-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydronaphthalen-1-yl)-amide, 2-{1-[2-(5-methyl-3-trifluoromethyl-pyrazole-1-yl)-acetylypiperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-methylphenyl)-2,3-dimethyl-isoxazolidin-3-yl]pyridine, 3-[5-(4-chloro-phenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxyacetamide;

L) Antifungal biocontrol agents, plant bioactivators: *Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Clyphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutna sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECOHOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB BioInnovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T.*

*viride* TV1 from Agribiotec srl, Italy), *Ulocladium oudemansii* HRU3 (e.g. BOTRY-ZEN® from Botry-Zen Ltd, NZ);

M) Growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxy-acetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzolenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chlorophenyl)-5-fluoro-pyridine-2-carboxylic acid, 4-amino-3-chloro-6-(4-chloro-2-fluoro-3-methoxyphenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The present invention furthermore relates to agrochemical compositions comprising a mixture of at least one compound I (component 1) and at least one further active substance useful for plant protection, e.g. selected from the groups A) to O) (component 2), in particular one further fungicide, e.g. one or more fungicide from the groups A) to L), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to L), as described above, is more efficient than combating those fungi with individual compounds I or individual fungicides from groups A) to L). By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I (component 1) and one further active substance (component 2), e.g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound I (component 1) and a first further active substance (component 2) and a second further active substance (component 3), e.g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

Preference is also given to mixtures comprising a compound I (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to mixtures comprising a compound of formula I (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to mixtures comprising a compound of formula I (component 1) and at least one active substance selected from group C) (component 2) and particularly selected from metalaxyl, (metalaxyl-M) mefenoxam, ofurace.

Preference is given to mixtures comprising a compound of formula I (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to mixtures comprising a compound I (component 1) and at least one active substance selected from group E) (component 2) and particularly selected from cyprodinil, mepanipyrim, pyrimethanil.

Preference is also given to mixtures comprising a compound I (component 1) and at least one active substance selected from group F) (component 2) and particularly selected from iprodione, fludioxonil, vinclozolin, quinoxyfen.

Preference is also given to mixtures comprising a compound I (component 1) and at least one active substance selected from group G) (component 2) and particularly selected from dimethomorph, flumorph, iprovalicarb, benthiavalicarb, mandipropamid, propamocarb.

Preference is also given to mixtures comprising a compound I (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising a compound I (component 1) and at least one active substance selected from group I) (component 2) and particularly selected from carpropamid and fenoxanil.

Preference is also given to mixtures comprising a compound I (component 1) and at least one active substance selected from group J) (component 2) and particularly selected from acibenzolar-5-methyl, probenazole, tiadinil, fosetyl, fosetyl-aluminium, $H_3PO_3$ and salts thereof.

Preference is also given to mixtures comprising a compound I (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Preference is also given to mixtures comprising a compound I (component 1) and at least one active substance selected from group L) (component 2) and particularly selected from *Bacillus subtilis* strain NRRL No. B-21661, *Bacillus pumilus* strain NRRL No. B-30087 and *Ulocladium oudemansii*.

Accordingly, the present invention furthermore relates to compositions comprising one compound I (component 1) and one further active substance (component 2), which further active substance is selected from the column "Component 2" of the lines B-1 to B-372 of Table B.

A further embodiment relates to the compositions B-1 to B-372 listed in Table B, where a row of Table B corresponds in each case to a fungicidal composition comprising one of the in the present specification individualized compounds of formula I (component 1) and the respective further active substance from groups A) to O) (component 2) stated in the row in question. Preferably, the compositions described comprise the active substances in synergistically effective amounts.

TABLE B

Composition comprising one indiviualized compound I and one further active substance from groups A) to O)

| Mixture | Component 1 | Component 2 |
| --- | --- | --- |
| B-1 | one individualized compound I | Azoxystrobin |
| B-2 | one individualized compound I | Coumethoxystrobin |
| B-3 | one individualized compound I | Coumoxystrobin |
| B-4 | one individualized compound I | Dimoxystrobin |
| B-5 | one individualized compound I | Enestroburin |
| B-6 | one individualized compound I | Fenaminstrobin |
| B-7 | one individualized compound I | Fenoxystrobin/Flufenoxystrobin |
| B-8 | one individualized compound I | Fluoxastrobin |
| B-9 | one individualized compound I | Kresoxim-methyl |
| B-10 | one individualized compound I | Metominostrobin |
| B-11 | one individualized compound I | Orysastrobin |
| B-12 | one individualized compound I | Picoxystrobin |
| B-13 | one individualized compound I | Pyraclostrobin |
| B-14 | one individualized compound I | Pyrametostrobin |
| B-15 | one individualized compound I | Pyraoxystrobin |
| B-16 | one individualized compound I | Pyribencarb |
| B-17 | one individualized compound I | Trifloxystrobin |
| B-18 | one individualized compound I | Triclopyricarb/Chlorodincarb |
| B-19 | one individualized compound I | 2-[2-(2,5-dimethyl-phenoxymethyl)-phenyl]-3-methoxy-acrylic acid methyl ester |
| B-20 | one individualized compound I | 2-(2-(3-(2,6-dichlorophenyl)-1-methyl-allylideneaminooxymethyl)-phenyl)-2-methoxyimino-N-methyl-acetamide |
| B-21 | one individualized compound I | Benalaxyl |
| B-22 | one individualized compound I | Benalaxyl-M |
| B-23 | one individualized compound I | Benodanil |
| B-24 | one individualized compound I | Bixafen |
| B-25 | one individualized compound I | Boscalid |
| B-26 | one individualized compound I | Carboxin |
| B-27 | one individualized compound I | Fenfuram |
| B-28 | one individualized compound I | Fenhexamid |
| B-29 | one individualized compound I | Flutolanil |
| B-30 | one individualized compound I | Fluxapyroxad |
| B-31 | one individualized compound I | Furametpyr |
| B-32 | one individualized compound I | Isopyrazam |
| B-33 | one individualized compound I | Isotianil |
| B-34 | one individualized compound I | Kiralaxyl |
| B-35 | one individualized compound I | Mepronil |
| B-36 | one individualized compound I | Metalaxyl |
| B-37 | one individualized compound I | Metalaxyl-M |
| B-38 | one individualized compound I | Ofurace |
| B-39 | one individualized compound I | Oxadixyl |
| B-40 | one individualized compound I | Oxycarboxin |
| B-41 | one individualized compound I | Penflufen |
| B-42 | one individualized compound I | Penthiopyrad |
| B-43 | one individualized compound I | Sedaxane |
| B-44 | one individualized compound I | Tecloftalam |
| B-45 | one individualized compound I | Thifluzamide |
| B-46 | one individualized compound I | Tiadinil |
| B-47 | one individualized compound I | 2-Amino-4-methyl-thiazole-5-carboxylic acid anilide |
| B-48 | one individualized compound I | N-(4'-trifluoromethylthiobiphenyl-2-yl)-3-difluoromethyl-1-methyl-1H-pyrazole-4-carboxamide |

TABLE B-continued

Composition comprising one indiviualized compound I
and one further active substance from groups A) to O)

| Mixture | Component 1 | Component 2 |
|---|---|---|
| B-49 | one individualized compound I | N-(2-(1,3,3-trimethyl-butyl)-phenyl)-1,3-dimethyl-5-fluoro-1H-pyrazole-4-carboxamide |
| B-50 | one individualized compound I | N-[9-(dichloromethylene)-1,2,3,4-tetrahydro-1,4-methanonaphthalen-5-yl]-3-(difluoromethyl)-1-methyl-1H-pyrazole-4-carboxamide |
| B-51 | one individualized compound I | 3-(difluoromethyl)-1-methyl-N-(1,1,3-trimethylindan-4-yl)pyrazole-4-carboxamide |
| B-52 | one individualized compound I | 3-(trifluoromethyl)-1-methyl-N-(1,1,3-trimethylindan-4-yl)pyrazole-4-carboxamide |
| B-53 | one individualized compound I | 1,3-dimethyl-N-(1,1,3-trimethylindan-4-yl)pyrazole-4-carboxamide |
| B-54 | one individualized compound I | 3-(trifluoromethyl)-1,5-dimethyl-N-(1,1,3-trimethylindan-4-yl)pyrazole-4-carboxamide |
| B-55 | one individualized compound I | 3-(difluoromethyl)-1,5-dimethyl-N-(1,1,3-trimethylindan-4-yl)pyrazole-4-carboxamide |
| B-56 | one individualized compound I | 1,3,5-trimethyl-N-(1,1,3-trimethylindan-4-yl)pyrazole-4-carboxamide |
| B-57 | one individualized compound I | Dimethomorph |
| B-58 | one individualized compound I | Flumorph |
| B-59 | one individualized compound I | Pyrimorph |
| B-60 | one individualized compound I | Flumetover |
| B-61 | one individualized compound I | Fluopicolide |
| B-62 | one individualized compound I | Fluopyram |
| B-63 | one individualized compound I | Zoxamide |
| B-64 | one individualized compound I | Carpropamid |
| B-65 | one individualized compound I | Diclocymet |
| B-66 | one individualized compound I | Mandipropamid |
| B-67 | one individualized compound I | Oxytetracyclin |
| B-68 | one individualized compound I | Silthiofam |
| B-69 | one individualized compound I | N-(6-methoxy-pyridin-3-yl) cyclopropanecarboxylic acid amide |
| B-70 | one individualized compound I | Azaconazole |
| B-71 | one individualized compound I | Bitertanol |
| B-72 | one individualized compound I | Bromuconazole |
| B-73 | one individualized compound I | Cyproconazole |
| B-74 | one individualized compound I | Difenoconazole |
| B-75 | one individualized compound I | Diniconazole |
| B-76 | one individualized compound I | Diniconazole-M |
| B-77 | one individualized compound I | Epoxiconazole |
| B-78 | one individualized compound I | Fenbuconazole |
| B-79 | one individualized compound I | Fluquinconazole |
| B-80 | one individualized compound I | Flusilazole |
| B-81 | one individualized compound I | Flutriafol |
| B-82 | one individualized compound I | Hexaconazol |
| B-83 | one individualized compound I | Imibenconazole |
| B-84 | one individualized compound I | Ipconazole |
| B-85 | one individualized compound I | Metconazole |
| B-86 | one individualized compound I | Myclobutanil |
| B-87 | one individualized compound I | Oxpoconazol |
| B-88 | one individualized compound I | Paclobutrazol |
| B-89 | one individualized compound I | Penconazole |
| B-90 | one individualized compound I | Propiconazole |
| B-91 | one individualized compound I | Prothioconazole |
| B-92 | one individualized compound I | Simeconazole |
| B-93 | one individualized compound I | Tebuconazole |
| B-94 | one individualized compound I | Tetraconazole |
| B-95 | one individualized compound I | Triadimefon |
| B-96 | one individualized compound I | Triadimenol |
| B-97 | one individualized compound I | Triticonazole |
| B-98 | one individualized compound I | Uniconazole |
| B-99 | one individualized compound I | 1-[rel-(2S;3R)-3-(2-chlorophenyl)-2-(2,4-difluorophenyl)-oxiranylmethyl]-5-thiocyanato-1H-[1,2,4]triazole, |
| B-100 | one individualized compound I | 2-[rel-(2S;3R)-3-(2-chlorophenyl)-2-(2,4-difluorophenyl)-oxiranylmethyl]-2H-[1,2,4]triazole-3-thiol |
| B-101 | one individualized compound I | Cyazofamid |
| B-102 | one individualized compound I | Amisulbrom |
| B-103 | one individualized compound I | Imazalil |

TABLE B-continued

Composition comprising one indiviualized compound I
and one further active substance from groups A) to O)

| Mixture | Component 1 | Component 2 |
| --- | --- | --- |
| B-104 | one individualized compound I | Imazalil-sulfate |
| B-105 | one individualized compound I | Pefurazoate |
| B-106 | one individualized compound I | Prochloraz |
| B-107 | one individualized compound I | Triflumizole |
| B-108 | one individualized compound I | Benomyl |
| B-109 | one individualized compound I | Carbendazim |
| B-110 | one individualized compound I | Fuberidazole |
| B-111 | one individualized compound I | Thiabendazole |
| B-112 | one individualized compound I | Ethaboxam |
| B-113 | one individualized compound I | Etridiazole |
| B-114 | one individualized compound I | Hymexazole |
| B-115 | one individualized compound I | 2-(4-Chloro-phenyl)-N-[4-(3,4-dimethoxy-phenyl)-isoxazol-5-yl]-2-prop-2-ynyloxy-acetamide |
| B-116 | one individualized compound I | Fluazinam |
| B-117 | one individualized compound I | Pyrifenox |
| B-118 | one individualized compound I | 3-[5-(4-Chloro-phenyl)-2,3-dimethyl-isoxazolidin-3-yl]-pyridine (Pyrisoxazole) |
| B-119 | one individualized compound I | 3-[5-(4-Methyl-phenyl)-2,3-dimethyl-isoxazolidin-3-yl]-pyridine |
| B-120 | one individualized compound I | Bupirimate |
| B-121 | one individualized compound I | Cyprodinil |
| B-122 | one individualized compound I | 5-Fluorocytosine |
| B-123 | one individualized compound I | 5-Fluoro-2-(p-tolylmethoxy)pyrimidin-4-amine |
| B-124 | one individualized compound I | 5-Fluoro-2-(4-fluorophenylmethoxy)-pyrimidin-4-amine |
| B-125 | one individualized compound I | Diflumetorim |
| B-126 | one individualized compound I | (5,8-Difluoroquinazolin-4-yl)-{2-[2-fluoro-4-(4-trifluoromethylpyridin-2-yloxy)-phenyl]-ethyl}-amine |
| B-127 | one individualized compound I | Fenarimol |
| B-128 | one individualized compound I | Ferimzone |
| B-129 | one individualized compound I | Mepanipyrim |
| B-130 | one individualized compound I | Nitrapyrin |
| B-131 | one individualized compound I | Nuarimol |
| B-132 | one individualized compound I | Pyrimethanil |
| B-133 | one individualized compound I | Triforine |
| B-134 | one individualized compound I | Fenpiclonil |
| B-135 | one individualized compound I | Fludioxonil |
| B-136 | one individualized compound I | Aldimorph |
| B-137 | one individualized compound I | Dodemorph |
| B-138 | one individualized compound I | Dodemorph-acetate |
| B-139 | one individualized compound I | Fenpropimorph |
| B-140 | one individualized compound I | Tridemorph |
| B-141 | one individualized compound I | Fenpropidin |
| B-142 | one individualized compound I | Fluoroimid |
| B-143 | one individualized compound I | Iprodione |
| B-144 | one individualized compound I | Procymidone |
| B-145 | one individualized compound I | Vinclozolin |
| B-146 | one individualized compound I | Famoxadone |
| B-147 | one individualized compound I | Fenamidone |
| B-148 | one individualized compound I | Flutianil |
| B-149 | one individualized compound I | Octhilinone |
| B-150 | one individualized compound I | Probenazole |
| B-151 | one individualized compound I | Fenpyrazamine |
| B-152 | one individualized compound I | Acibenzolar-S-methyl |
| B-153 | one individualized compound I | Ametoctradin |
| B-154 | one individualized compound I | Amisulbrom |
| B-155 | one individualized compound I | [(3S,6S,7R,8R)-8-benzyl-3-[(3-isobutyryloxymethoxy-4-methoxypyridine-2-carbonyl)amino]-6-methyl-4,9-dioxo-[1,5]dioxonan-7-yl] 2-methylpropanoate |
| B-156 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate |
| B-157 | one individualized compound I | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate |
| B-158 | one individualized compound I | [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate |

TABLE B-continued

Composition comprising one indiviualized compound I
and one further active substance from groups A) to O)

| Mixture | Component 1 | Component 2 |
| --- | --- | --- |
| B-159 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| B-160 | one individualized compound I | (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| B-161 | one individualized compound I | Anilazin |
| B-162 | one individualized compound I | Blasticidin-S |
| B-163 | one individualized compound I | Captafol |
| B-164 | one individualized compound I | Captan |
| B-165 | one individualized compound I | Chinomethionat |
| B-166 | one individualized compound I | Dazomet |
| B-167 | one individualized compound I | Debacarb |
| B-168 | one individualized compound I | Diclomezine |
| B-169 | one individualized compound I | Difenzoquat, |
| B-170 | one individualized compound I | Difenzoquat-methylsulfate |
| B-171 | one individualized compound I | Fenoxanil |
| B-172 | one individualized compound I | Folpet |
| B-173 | one individualized compound I | Oxolinsäure |
| B-174 | one individualized compound I | Piperalin |
| B-175 | one individualized compound I | Proquinazid |
| B-176 | one individualized compound I | Pyroquilon |
| B-177 | one individualized compound I | Quinoxyfen |
| B-178 | one individualized compound I | Triazoxid |
| B-179 | one individualized compound I | Tricyclazole |
| B-180 | one individualized compound I | 2-Butoxy-6-iodo-3-propyl-chromen-4-one |
| B-181 | one individualized compound I | 5-Chloro-1-(4,6-dimethoxy-pyrimidin-2-yl)-2-methyl-1H-benzoimidazole |
| B-182 | one individualized compound I | 5-Chloro-7-(4-methyl-piperidin-1-yl)-6-(2,4,6-trifluoro-phenyl)-[1,2,4]triazolo[1,5-a]pyrimidine |
| B-183 | one individualized compound I | Ferbam |
| B-184 | one individualized compound I | Mancozeb |
| B-185 | one individualized compound I | Maneb |
| B-186 | one individualized compound I | Metam |
| B-187 | one individualized compound I | Methasulphocarb |
| B-188 | one individualized compound I | Metiram |
| B-189 | one individualized compound I | Propineb |
| B-190 | one individualized compound I | Thiram |
| B-191 | one individualized compound I | Zineb |
| B-192 | one individualized compound I | Ziram |
| B-193 | one individualized compound I | Diethofencarb |
| B-194 | one individualized compound I | Benthiavalicarb |
| B-195 | one individualized compound I | Iprovalicarb |
| B-196 | one individualized compound I | Propamocarb |
| B-197 | one individualized compound I | Propamocarb hydrochlorid |
| B-198 | one individualized compound I | Valifenalate |
| B-199 | one individualized compound I | N-(1-(1-(4-cyanophenyl)ethanesulfonyl)-but-2-yl) carbamic acid-(4-fluoro-phenyl) ester |
| B-200 | one individualized compound I | Dodine |
| B-201 | one individualized compound I | Dodine free base |
| B-202 | one individualized compound I | Guazatine |
| B-203 | one individualized compound I | Guazatine-acetate |
| B-204 | one individualized compound I | Iminoctadine |
| B-205 | one individualized compound I | Iminoctadine-triacetate |
| B-206 | one individualized compound I | Iminoctadine-tris(albesilate) |
| B-207 | one individualized compound I | Kasugamycin |
| B-208 | one individualized compound I | Kasugamycin-hydrochloride-hydrate |
| B-209 | one individualized compound I | Polyoxine |
| B-210 | one individualized compound I | Streptomycin |
| B-211 | one individualized compound I | Validamycin A |
| B-212 | one individualized compound I | Binapacryl |
| B-213 | one individualized compound I | Dicloran |
| B-214 | one individualized compound I | Dinobuton |
| B-215 | one individualized compound I | Dinocap |
| B-216 | one individualized compound I | Nitrothal-isopropyl |
| B-217 | one individualized compound I | Tecnazen |
| B-218 | one individualized compound I | Fentin salts |
| B-219 | one individualized compound I | Dithianon |

TABLE B-continued

Composition comprising one indiviualized compound I
and one further active substance from groups A) to O)

| Mixture | Component 1 | Component 2 |
| --- | --- | --- |
| B-220 | one individualized compound I | 2,6-dimethyl-1H,5H-[1,4]dithiino[2,3-c:5,6-c']dipyrrole-1,3,5,7(2H,6H)-tetraone |
| B-221 | one individualized compound I | Isoprothiolane |
| B-222 | one individualized compound I | Edifenphos |
| B-223 | one individualized compound I | Fosetyl, Fosetyl-aluminium |
| B-224 | one individualized compound I | Iprobenfos |
| B-225 | one individualized compound I | Phosphorous acid ($H_3PO_3$) and derivatives |
| B-226 | one individualized compound I | Pyrazophos |
| B-227 | one individualized compound I | Tolclofos-methyl |
| B-228 | one individualized compound I | Chlorothalonil |
| B-229 | one individualized compound I | Dichlofluanid |
| B-230 | one individualized compound I | Dichlorophen |
| B-231 | one individualized compound I | Flusulfamide |
| B-232 | one individualized compound I | Hexachlorbenzene |
| B-233 | one individualized compound I | Pencycuron |
| B-234 | one individualized compound I | Pentachlorophenol and salts |
| B-235 | one individualized compound I | Phthalide |
| B-236 | one individualized compound I | Quintozene |
| B-237 | one individualized compound I | Thiophanate Methyl |
| B-238 | one individualized compound I | Tolylfluanid |
| B-239 | one individualized compound I | N-(4-chloro-2-nitro-phenyl)-N-ethyl-4-methyl-benzenesulfonamide |
| B-240 | one individualized compound I | Bordeaux mixture |
| B-241 | one individualized compound I | Copper acetate |
| B-242 | one individualized compound I | Copper hydroxide |
| B-243 | one individualized compound I | Copper oxychloride |
| B-244 | one individualized compound I | basic Copper sulfate |
| B-245 | one individualized compound I | Sulfur |
| B-246 | one individualized compound I | Biphenyl |
| B-247 | one individualized compound I | Bronopol |
| B-248 | one individualized compound I | Cyflufenamid |
| B-249 | one individualized compound I | Cymoxanil |
| B-250 | one individualized compound I | Diphenylamin |
| B-251 | one individualized compound I | Metrafenone |
| B-252 | one individualized compound I | Pyriofenone |
| B-253 | one individualized compound I | Mildiomycin |
| B-254 | one individualized compound I | Oxin-copper |
| B-255 | one individualized compound I | Prohexadione calcium |
| B-256 | one individualized compound I | Spiroxamine |
| B-257 | one individualized compound I | Tebufloquin |
| B-258 | one individualized compound I | Tolylfluanid |
| B-259 | one individualized compound I | N-(Cyclopropylmethoxyimino-(6-difluoromethoxy-2,3-difluoro-phenyl)-methyl)-2-phenyl acetamide |
| B-260 | one individualized compound I | N'-(4-(4-chloro-3-trifluoromethyl-phenoxy)-2,5-dimethyl-phenyl)-N-ethyl-N-methyl formamidine |
| B-261 | one individualized compound I | N'-(4-(4-fluoro-3-trifluoromethyl-phenoxy)-2,5-dimethyl-phenyl)-N-ethyl-N-methyl formamidine |
| B-262 | one individualized compound I | N'-(2-methyl-5-trifluoromethyl-4-(3-trimethylsilanyl-propoxy)-phenyl)-N-ethyl-N-methyl formamidine |
| B-263 | one individualized compound I | N'-(5-difluoromethyl-2-methyl-4-(3-trimethylsilanyl-propoxy)-phenyl)-N-ethyl-N-methyl formamidine |
| B-264 | one individualized compound I | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-265 | one individualized compound I | 2-{1-[2-(5-Methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide |
| B-266 | one individualized compound I | 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone |
| B-267 | one individualized compound I | Methoxy-acetic acid 6-tert-butyl-8-fluoro-2,3-dimethyl-quinolin-4-yl ester |

TABLE B-continued

Composition comprising one indiviualized compound I
and one further active substance from groups A) to O)

| Mixture | Component 1 | Component 2 |
| --- | --- | --- |
| B-268 | one individualized compound I | N-Methyl-2-{1-[(5-methyl-3-trifluoro-methyl-1H-pyrazol-1-yl)-acetyl]-piperidin-4-yl}-N-[(1R)-1,2,3,4-tetrahydro-naphthalen-1-yl]-4-thiazolecarboxamide |
| B-269 | one individualized compound I | *Bacillus subtilis* NRRL No. B-21661 |
| B-270 | one individualized compound I | *Bacillus pumilus* NRRL No. B-30087 |
| B-271 | one individualized compound I | *Ulocladium oudemansii* |
| B-272 | one individualized compound I | Carbaryl |
| B-273 | one individualized compound I | Carbofuran |
| B-274 | one individualized compound I | Carbosulfan |
| B-275 | one individualized compound I | Methomylthiodicarb |
| B-276 | one individualized compound I | Bifenthrin |
| B-277 | one individualized compound I | Cyfluthrin |
| B-278 | one individualized compound I | Cypermethrin |
| B-279 | one individualized compound I | alpha-Cypermethrin |
| B-280 | one individualized compound I | zeta-Cypermethrin |
| B-281 | one individualized compound I | Deltamethrin |
| B-282 | one individualized compound I | Esfenvalerate |
| B-283 | one individualized compound I | Lambda-cyhalothrin |
| B-284 | one individualized compound I | Permethrin |
| B-285 | one individualized compound I | Tefluthrin |
| B-286 | one individualized compound I | Diflubenzuron |
| B-287 | one individualized compound I | Flufenoxuron |
| B-288 | one individualized compound I | Lufenuron |
| B-289 | one individualized compound I | Teflubenzuron |
| B-290 | one individualized compound I | Spirotetramate |
| B-291 | one individualized compound I | Clothianidin |
| B-292 | one individualized compound I | Dinotefuran |
| B-293 | one individualized compound I | Imidacloprid |
| B-294 | one individualized compound I | Thiamethoxam |
| B-295 | one individualized compound I | Flupyradifurone |
| B-296 | one individualized compound I | Acetamiprid |
| B-297 | one individualized compound I | Thiacloprid |
| B-298 | one individualized compound I | Endosulfan |
| B-299 | one individualized compound I | Fipronil |
| B-300 | one individualized compound I | Abamectin |
| B-301 | one individualized compound I | Emamectin |
| B-302 | one individualized compound I | Spinosad |
| B-303 | one individualized compound I | Spinetoram |
| B-304 | one individualized compound I | Hydramethylnon |
| B-305 | one individualized compound I | Chlorfenapyr |
| B-306 | one individualized compound I | Fenbutatin oxide |
| B-307 | one individualized compound I | Indoxacarb |
| B-308 | one individualized compound I | Metaflumizone |
| B-309 | one individualized compound I | Flonicamid |
| B-310 | one individualized compound I | Lubendiamide |
| B-311 | one individualized compound I | Chlorantraniliprole |
| B-312 | one individualized compound I | Cyazypyr (HGW86) |
| B-313 | one individualized compound I | Cyflumetofen |
| B-314 | one individualized compound I | Acetochlor |
| B-315 | one individualized compound I | Dimethenamid |
| B-316 | one individualized compound I | metolachlor |
| B-317 | one individualized compound I | Metazachlor |
| B-318 | one individualized compound I | Glyphosate |
| B-319 | one individualized compound I | Glufosinate |
| B-320 | one individualized compound I | Sulfosate |
| B-321 | one individualized compound I | Clodinafop |
| B-322 | one individualized compound I | Fenoxaprop |
| B-323 | one individualized compound I | Fluazifop |
| B-324 | one individualized compound I | Haloxyfop |
| B-325 | one individualized compound I | Paraquat |
| B-326 | one individualized compound I | Phenmedipham |
| B-327 | one individualized compound I | Clethodim |
| B-328 | one individualized compound I | Cycloxydim |
| B-329 | one individualized compound I | Profoxydim |
| B-330 | one individualized compound I | Sethoxydim |
| B-331 | one individualized compound I | Tepraloxydim |
| B-332 | one individualized compound I | Pendimethalin |
| B-333 | one individualized compound I | Prodiamine |
| B-334 | one individualized compound I | Trifluralin |
| B-335 | one individualized compound I | Acifluorfen |
| B-336 | one individualized compound I | Bromoxynil |
| B-337 | one individualized compound I | Imazamethabenz |
| B-338 | one individualized compound I | Imazamox |
| B-339 | one individualized compound I | Imazapic |

TABLE B-continued

Composition comprising one indiviualized compound I
and one further active substance from groups A) to O)

| Mixture | Component 1 | Component 2 |
|---|---|---|
| B-340 | one individualized compound I | Imazapyr |
| B-341 | one individualized compound I | Imazaquin |
| B-342 | one individualized compound I | Imazethapyr |
| B-343 | one individualized compound I | 2,4-Dichlorophenoxyacetic acid (2,4-D) |
| B-344 | one individualized compound I | Chloridazon |
| B-345 | one individualized compound I | Clopyralid |
| B-346 | one individualized compound I | Fluroxypyr |
| B-347 | one individualized compound I | Picloram |
| B-348 | one individualized compound I | Picolinafen |
| B-349 | one individualized compound I | Bensulfuron |
| B-350 | one individualized compound I | Chlorimuron-ethyl |
| B-351 | one individualized compound I | Cyclosulfamuron |
| B-352 | one individualized compound I | Iodosulfuron |
| B-353 | one individualized compound I | Mesosulfuron |
| B-354 | one individualized compound I | Metsulfuron-methyl |
| B-355 | one individualized compound I | Nicosulfuron |
| B-356 | one individualized compound I | Rimsulfuron |
| B-357 | one individualized compound I | Triflusulfuron |
| B-358 | one individualized compound I | Atrazine |
| B-359 | one individualized compound I | Hexazinone |
| B-360 | one individualized compound I | Diuron |
| B-361 | one individualized compound I | Florasulam |
| B-362 | one individualized compound I | Pyroxasulfone |
| B-363 | one individualized compound I | Bentazone |
| B-364 | one individualized compound I | Cinidon-ethyl |
| B-365 | one individualized compound I | Cinmethylin |
| B-366 | one individualized compound I | Dicamba |
| B-367 | one individualized compound I | Diflufenzopyr |
| B-368 | one individualized compound I | Quinclorac |
| B-369 | one individualized compound I | Quinmerac |
| B-370 | one individualized compound I | Mesotrione |
| B-371 | one individualized compound I | Saflufenacil |
| B-372 | one individualized compound I | Topramezone |

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028,657).

The mixtures of active substances can be prepared as compositions comprising besides the active ingredients at least one inert ingredient by usual means, e.g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

SYNTHESIS EXAMPLES

With due modification of the starting compounds, the procedures shown in the synthesis examples below were used to obtain further compounds I. The resulting compounds, together with physical data, are listed in Table I below.

I. Preparation of compounds I

I.1 Preparation of 2,6-dimethyl-[1,4]benzodithiino[2,3-c]pyrrole-1,3-dione (ex. I-2)

A stirred solution of 4-methylbenzene-1,2-dithiol (0.5 g) in anhydrous DMF (50 ml) was treated with $K_2CO_3$ and 3,4-dichloro-1-methyl-pyrrole-2,5-dione (0.73 g) and stirred for about 7 hours at 80° C. The reaction mixture was poured into water and extracted with MTBE. The combined organic phases were washed once with water and after removal of the solvent under reduced pressure the crude product (0.85 g) was purified by flash column chromatography on silica gel (cyclohexane/ethyl acetate 9:1) to yield the compound ex. I-2 (0.25 g); m.p.: 171-176° C.

TABLE I

Compounds of formulae I.A to I.G.

| ex. no | Form. | $R^1$ | $R^{2a}$ | $R^{2b}$ | $R^{2c}$ | $R^{2d}$ | Phys.-chem. Data: m.p. [° C.]; NMR |
|---|---|---|---|---|---|---|---|
| I-1 | I.A | $CH_2CH_3$ | H | H | H | H | 107-110° C. |
| I-2 | I.A | $CH_3$ | H | H | $CH_3$ | H | 171-176° C. |
| I-3 | I.A | $OCH_3$ | H | H | $CH_3$ | H | NMR (CDCl$_3$): 2.3 (s, 3H); 3.8 (s, 3H) ppm |
| I-4 | I.A | $CH_3$ | Cl | H | H | Cl | 199° C. |
| I-5 | I.G | $CH_2CH_3$ | H | H | H | H | 190-195° C. | m.p. = melting point.

III. Examples of the Action Against Harmful Fungi

The fungicidal action of the compounds of the formula I was demonstrated by the following experiments:

A) Microtiter Tests

The active substances were formulated separately as a stock solution in dimethyl sulfoxide (DMSO) at a concentration of 10 000 ppm.

Use Example 1

Activity Against the Rice Blast Pathogen *Pyricularia oryzae*

The stock solution was pipetted into a microtiter plate (MTP) and diluted to the stated active substance concentration using an aequous biomalt—or yeast—beactopeptonesodium acetate solution. An aqueous spore suspension of *Pyricularia oryzae* was then added. The plates were placed in a water vapor-saturated chamber at temperatures of 18° C. Using an absorption photometer, the microtiter plates were measured at 405 nm on day 7 after the inoculation. The measured parameters were compared to the growth of the active substance-free control variant (=100%) and the fungus- and active substance-free blank value to determine the relative growth in % of the pathogens in the individual active substances.

In this test, the sample which had been treated with 125 ppm of the active substance from example I-1 showed up to at most 5% growth of the pathogen.

Use Example 2

Activity Against the Grey Mold Pathogen *Botrytis cinerea*

The stock solution was pipetted into a microtiter plate (MTP) and diluted to the stated active substance concentration using an aequous biomalt—or yeast—beactopeptonesodium acetate solution. An aqueous spore suspension of *Botrytis cinerea* was then added. The plates were placed in a water vapor-saturated chamber at temperatures of 18° C. Using an absorption photometer, the microtiter plates were measured at 405 nm on day 7 after the inoculation. The measured parameters were compared to the growth of the active substance-free control variant (=100%) and the fungus- and active substance-free blank value to determine the relative growth in % of the pathogens in the individual active substances.

In this test, the sample which had been treated with 125 ppm of the active substance from examples I-1 showed up to at most 5% growth of the pathogen.

B) Greenhouse Tests

The stock solution were prepared: a mixture of acetone and/or dimethylsulfoxide and the wetting agent/emulsifier Wettol, which is based on ethoxylated alkylphenoles, in a relation solvent-emulsifier of 99 to 1 (v/v) was added to 25 mg of the compound to give a total of 5 ml. Water was then added to total volume of 100 ml.

This stock solution was diluted with the described solvent-emulsifier-water mixture to the given concentration.

Use Example 3

Preventative Control of Leaf Blotch on Wheat Caused by *Septoria tritici*

Leaves of pot-grown wheat seedling were sprayed to run-off with an aqueous suspension of the active compound or their mixture, prepared as described. The plants were allowed to air-dry. At the following day the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area.

In this test, the plants which had been treated with 1000 ppm of the active substance from example I-3 showed an infection of less than or equal to 5% whereas the untreated plants were 90% infected.

The invention claimed is:

1. A method for combating harmful fungi, comprising: treating the fungi or the materials, plants, the soil or seeds to be protected against fungal attack with an effective amount of at least one compound of formula I

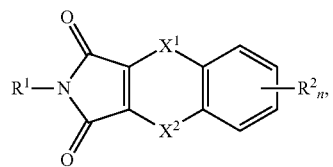

wherein:
$X^1$ is S, S=O, O or NR;
$X^2$ is S, O or NR;
R is hydrogen, $NR^A R^B$, OH, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio,
$C_3$-$C_6$-cycloalkyl, $C_3$-$C_6$-cycloalkenyl, $C_3$-$C_6$-cycloalkyl-$C_1$-$C_6$-alkyl, $C_2$-$C_6$-alkenyl, $C_1$-$C_6$-alkylcarbonyl or phenyl;
$R^A, R^B$ independently of one another are hydrogen, $C_1$-$C_6$-alkyl,
$C_2$-$C_6$-alkenyl, $C_2$-$C_6$-alkynyl, $C_3$-$C_6$-cycloalkyl, $C_3$-$C_6$-cycloalkenyl, $C_1$-$C_6$-alkylcarbonyl, $C_1$-$C_6$-alkenylcarbonyl,
$C_1$-$C_6$-alkynylcarbonyl, $C_1$-$C_6$-alkoxycarbonyl, $C_1$-$C_6$-alkenyloxycarbonyl, $C_1$-$C_6$-alkynyloxycarbonyl, $C_1$-$C_6$-alkylaminocarbonyl, di($C_1$-$C_6$-alkyl)aminocarbonyl, $C_1$-$C_6$-alkenylaminocarbonyl or $C_1$-$C_6$-alkynylaminocarbonyl;

$R^1$ is hydrogen, OH, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio, $C_3$-$C_6$-cycloalkyl, $C_3$-$C_6$-cycloalkenyl, $C_3$-$C_6$-cycloalkyl-$C_1$-$C_6$-alkyl, $C_2$-$C_6$-alkenyl or $C_1$-$C_6$-alkylcarbonyl;

$R^2$ is halogen, OH, CN, nitro, $C_1$-$C_6$-alkyl, $C_1$-$C_6$-alkoxy, $C_3$-$C_6$-cycloalkyl, $C_3$-$C_6$-cycloalkenyl, $C_3$-$C_6$-cycloalkyl-$C_1$-$C_6$-alkyl, $C_2$-$C_6$-alkenyl, $C_2$-$C_6$-alkynyl, $C_1$-$C_6$-alkylcarbonyl, $C_1$-$C_6$-alkenylcarbonyl, $C_1$-$C_6$-alkynylcarbonyl, $C_1$-$C_6$-alkoxycarbonyl, $C_1$-$C_6$-alkenyloxycarbonyl, $C_1$-$C_6$-alkynyloxycarbonyl, $C_1$-$C_6$-alkylaminocarbonyl, di($C_1$-$C_6$-alkyl)aminocarbonyl, $C_1$-$C_6$-alkenylaminocarbonyl or $C_1$-$C_6$-alkynylaminocarbonyl or phenyl;

n is an integer between 0 and 4, wherein the aliphatic and cyclic groups R, $R^1$ and $R^2$ may carry 1, 2, 3, 4 or up to the maximum possible number of identical or different groups $R^a$:

$R^a$ is amino, halogen, hydroxyl, nitro, CN, carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_8$-cycloalkenyl, $C_1$-$C_6$-alkylamino, $C_1$-$C_4$-alkylcarbonyl, $C_1$-$C_4$-alkoxycarbonyl, $C_1$-$C_4$-alkylcarbonyloxy or $NR^A R^B$;

or an N-oxide or an agriculturally acceptable salt thereof.

2. The method of claim 1, wherein $X^1$ and $X^2$ together cannot be NR and S.

3. The method of claim 1, wherein $X^1$ and $X^2$ together cannot be NR and O.

4. The method of claim 1, wherein $X^1$ and $X^2$ are identical.

5. The method of claim 4, wherein $X^1$ and $X^2$ are S.

6. The method of claim 1, wherein $R^1$ is selected from the group consisting of hydrogen, $C_1$-$C_6$-alkyl and $C_1$-$C_6$-alkoxy.

7. The method of claim 1, wherein n is selected from 0, 1 and 2.

8. The method of claim 1, wherein $R^2$ is selected from the group consisting of hydrogen, halogen, CN, nitro, $C_1$-$C_6$-alkyl and $C_1$-$C_6$-halogenalkyl.

* * * * *